United States Patent
Matsuda et al.

(10) Patent No.: US 7,227,161 B2
(45) Date of Patent: Jun. 5, 2007

(54) PARTICLE BEAM IRRADIATION APPARATUS, TREATMENT PLANNING UNIT, AND PARTICLE BEAM IRRADIATION METHOD

(75) Inventors: Koji Matsuda, Hitachi (JP); Takahide Nakayama, Nara (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/236,688

(22) Filed: Sep. 28, 2005

(65) Prior Publication Data

US 2006/0022153 A1 Feb. 2, 2006

Related U.S. Application Data

(62) Division of application No. 10/842,463, filed on May 11, 2004.

(51) Int. Cl.
  *G21G 5/00* (2006.01)
(52) U.S. Cl. ............................ 250/492.3; 250/492.1
(58) Field of Classification Search .............. 250/492.3
  See application file for complete search history.

(56) References Cited

U.S. PATENT DOCUMENTS

| 5,017,789 A | 5/1991 | Young et al. |
| 5,363,008 A | 11/1994 | Hiramoto et al. |
| 6,265,837 B1 * | 7/2001 | Akiyama et al. ........... 315/503 |
| 6,509,573 B1 * | 1/2003 | Badura et al. ........... 250/492.3 |

FOREIGN PATENT DOCUMENTS

| EP | 0 779 081 | 6/1997 |
| EP | 0 779 081 A2 | 6/1997 |
| JP | 9-099108 | 4/1997 |
| JP | 09-223600 | 8/1997 |
| JP | 09-253226 | 9/1997 |
| JP | 10-071214 | 3/1998 |
| JP | 2833602 | 10/1998 |
| JP | 10-314323 | 12/1998 |
| JP | 2000-162391 | 6/2000 |
| JP | 2001-340475 | 12/2001 |
| JP | 2003-126278 | 5/2003 |
| WO | WO 00/48680 | 8/2000 |

(Continued)

OTHER PUBLICATIONS

W. T. Chu et al., "Instrumentation for treatment for cancer using proton and light-ion beams", Review of Scientific Instruments, Aug. 1993, p. 64, Woodbury, NY.

(Continued)

*Primary Examiner*—David A. Vanore
(74) *Attorney, Agent, or Firm*—Dickstein Shapiro LLP

(57) ABSTRACT

A particle beam irradiation apparatus includes a synchrotron, two scanning electromagnets, an beam delivery apparatus for outputting an ion beam extracted from the synchrotron, and an accelerator and transport system controller, and a scanning controller. These controllers stop the output of the ion beam from the beam delivery apparatus; in a state where the output of the ion beam is stopped, change the irradiation position of the ion beam by controlling the scanning electromagnets; and after this change, control the scanning electromagnets to start the output of the ion beam from the beam delivery apparatus and to perform irradiations of the ion beam to at least one irradiation position a plurality of times based on treatment planning information.

14 Claims, 17 Drawing Sheets

FOREIGN PATENT DOCUMENTS

| WO | WO 00/62307 | 10/2000 |
| WO | WO 02/41948 A1 | 5/2002 |
| WO | WO 03/069634 A2 | 8/2003 |

OTHER PUBLICATIONS

Takuji Furukawa et al., "Fast beam cut-off method in RF-knockout extraction for spot-scanning", Nuclear Instruments and Methods in Physics, vol. A, No. 489, 2002, p. 59-67.

T. Furukawa et al., "Characteristics of fast beam switching for spot scanning", Nuclear Instruments and Methods in Physics, vol. A, No. 503, 2003, p. 485-495.

Tatsuaki Kanai et al., "Spot scanning system for proton radiotherapy", National Institute of Radiological Sciences, vol. 7, No. 4, Aug. 1980, p. 365-369.

T. Harberer et al., "Magnetic scanning system for heavy ion therapy", Nuclear Instruments and Methods in Physics, vol. A, No. 330, 1993, p. 296-305.

W. T. Chu et al., "Instrumentation for Treatment of Cancer Using Proton and Light-Ion Beams," Review of Scientific Instruments, American Institute of Physics, New York, vol. 64, No. 8, Aug. 1, 1993, pp. 2055-2122.

T. Kanai et al., "Spot Scanning System for Proton Radiotherapy," Medical Physics, vol. 7, No. 4, Aug. 1980, pp. 365-369.

T. Haberer et al., "Magnetic Scanning System for Heavy Ion Therapy," Nuclear Instruments & Methods in Physics Research, Section—A: Accelerators, Spectrometers, Detectors and Associated Equipment, North-Holland Publishing Company, vol. A330, No. 1/2, Jun. 10, 1993, pp. 296-305.

* cited by examiner

FIG.7

| LAYER NUMBER | IRRADIATION DOSE BEFORE DIVISION | NUMBER OF TIMES OF DIVISION | IRRADIATION DOSE AFTER DIVISION |
|---|---|---|---|
| 1 | 70 | 7 | 10 |
| 2 | 25 | 3 | 8.3 |
| 3 | 17.9 | 3 | 9 |
| 4 | 12.6 | 2 | 6.3 |

FIG.8

| | 1-ST TIME | 2-ND TIME | 3-RD TIME | 4-TH TIME | 5-TH TIME | 6-TH TIME | 7-TH TIME |
|---|---|---|---|---|---|---|---|
| LAYER 1 | 10 | 10 | 10 | 10 | 10 | 10 | 10 |
| LAYER 2 | 8.3 | 8.3 | 8.3 | | | | |
| LAYER 3 | 10 9.0 | 10 9.0 | 10 | 10 | 10 | 10 | 10 |
| LAYER 4 | 8.3 6.3 | 8.3 6.3 | 8.3 | | | | |

FIG.11

| LAYER (LAYER NO. -IRRADIATION NO.) | X-POSITION | Y-POSITION | IRRADIATION DOSE | LAYER CHANGE FLAG |
|---|---|---|---|---|
| ⋮ | ⋮ | ⋮ | ⋮ | ⋮ |
| 2-2 | 10 | 2.5 | 8.3 | 0 |
| 2-2 | 9 | 2.5 | 8.3 | 0 |
| 2-2 | 8 | 2.5 | 8.3 | 0 |
| ⋮ | ⋮ | ⋮ | ⋮ | ⋮ |
| 2-2 | 2 | 2.5 | 8.3 | 0 |
| 2-2 | 1 | 2.5 | 8.3 | 0 |
| 2-2 | 1 | 3.5 | 8.3 | 0 |
| ⋮ | ⋮ | ⋮ | ⋮ | ⋮ |
| 2-2 | 10 | 3.5 | 8.3 | 0 |
| 2-2 | 10 | 4.5 | 8.3 | 0 |
| ⋮ | ⋮ | ⋮ | ⋮ | ⋮ |
| 2-2 | 1 | 4.5 | 8.3 | 0 |
| 2-3 | 10 | 2.5 | 8.3 | 0 |
| 2-3 | 9 | 2.5 | 8.3 | 0 |
| 2-3 | 8 | 2.5 | 8.3 | 0 |
| ⋮ | ⋮ | ⋮ | ⋮ | ⋮ |
| 2-3 | 2 | 2.5 | 8.3 | 0 |
| 2-3 | 1 | 2.5 | 8.3 | 0 |
| 2-3 | 1 | 3.5 | 8.3 | 0 |
| ⋮ | ⋮ | ⋮ | ⋮ | ⋮ |
| 2-3 | 10 | 3.5 | 8.3 | 0 |
| 2-3 | 10 | 4.5 | 8.3 | 0 |
| ⋮ | ⋮ | ⋮ | ⋮ | ⋮ |
| 2-3 | 1 | 4.5 | 8.3 | 1 |
| 3-1 | -10 | -4.5 | 10 | 0 |
| ⋮ | ⋮ | ⋮ | ⋮ | ⋮ |
| 3-1 | 0 | -4.5 | 10 | 0 |
| 3-1 | 1 | -4.5 | 9 | 0 |
| ⋮ | ⋮ | ⋮ | ⋮ | ⋮ |
| 3-1 | 10 | -3.5 | 9 | 0 |
| 3-1 | 9 | -3.5 | 9 | 0 |
| ⋮ | ⋮ | ⋮ | ⋮ | ⋮ |
| 3-1 | 10 | -4.5 | 9 | 0 |
| ⋮ | ⋮ | ⋮ | ⋮ | ⋮ |

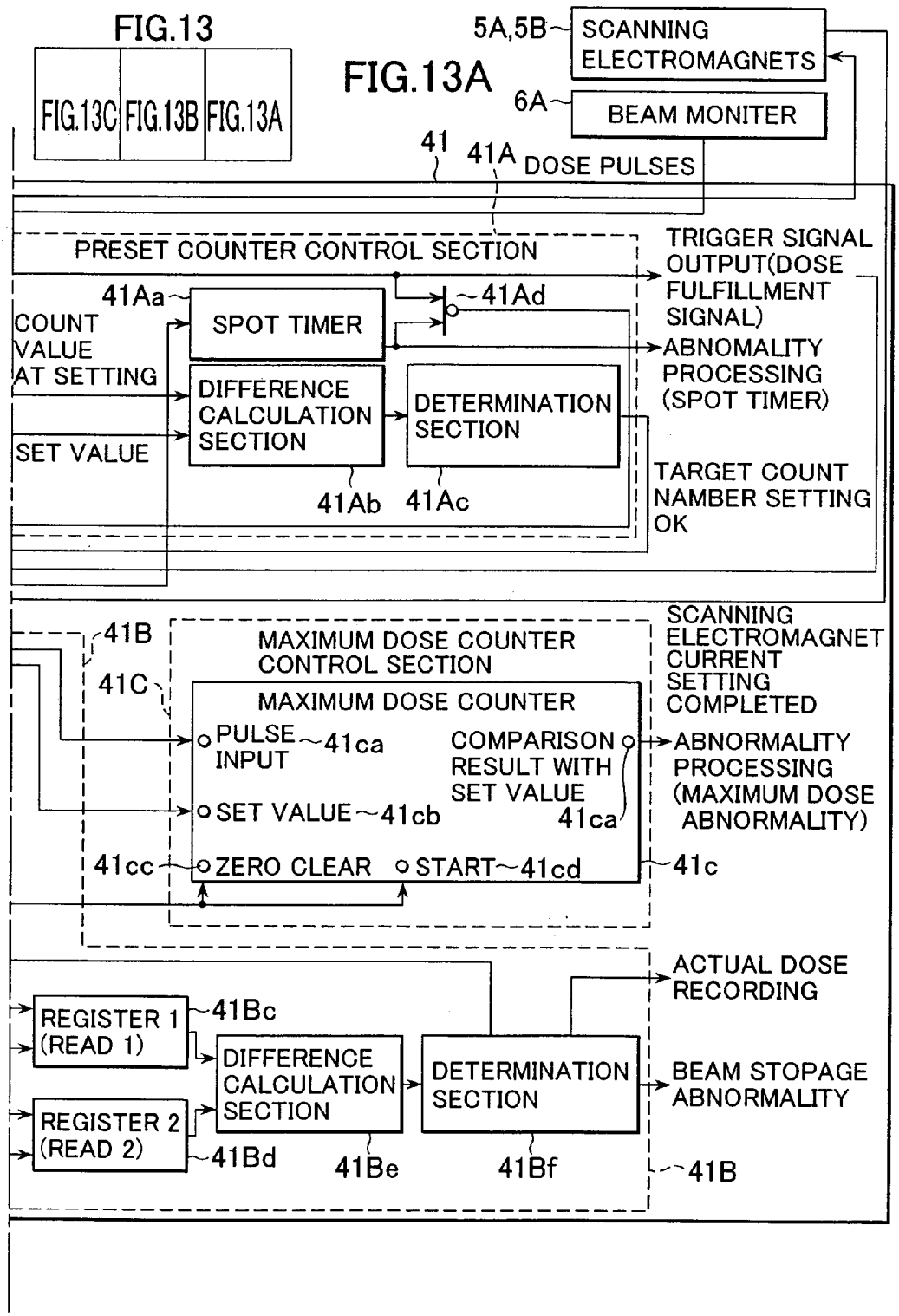

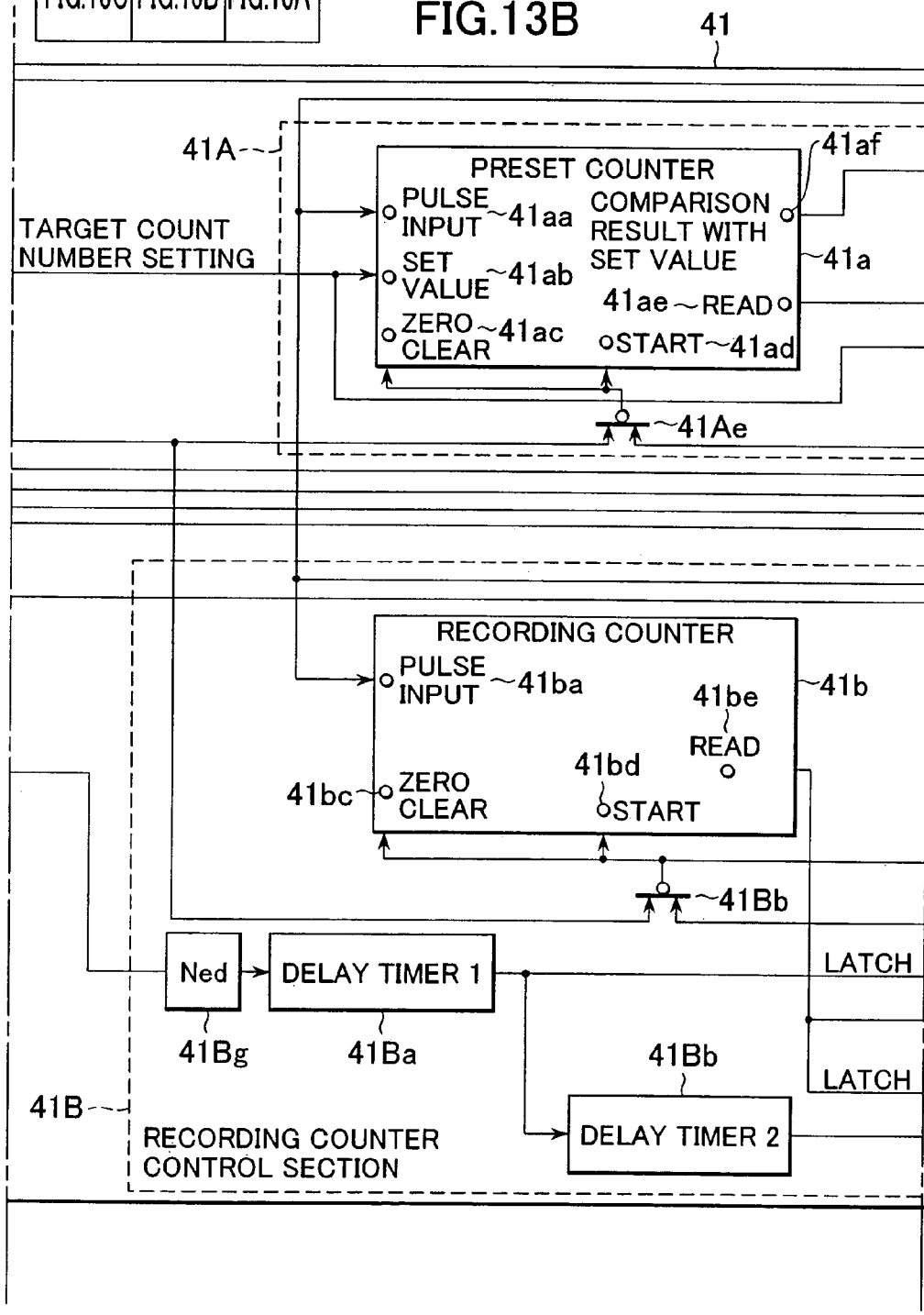

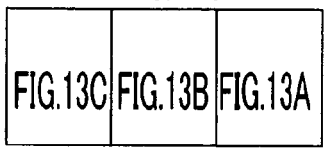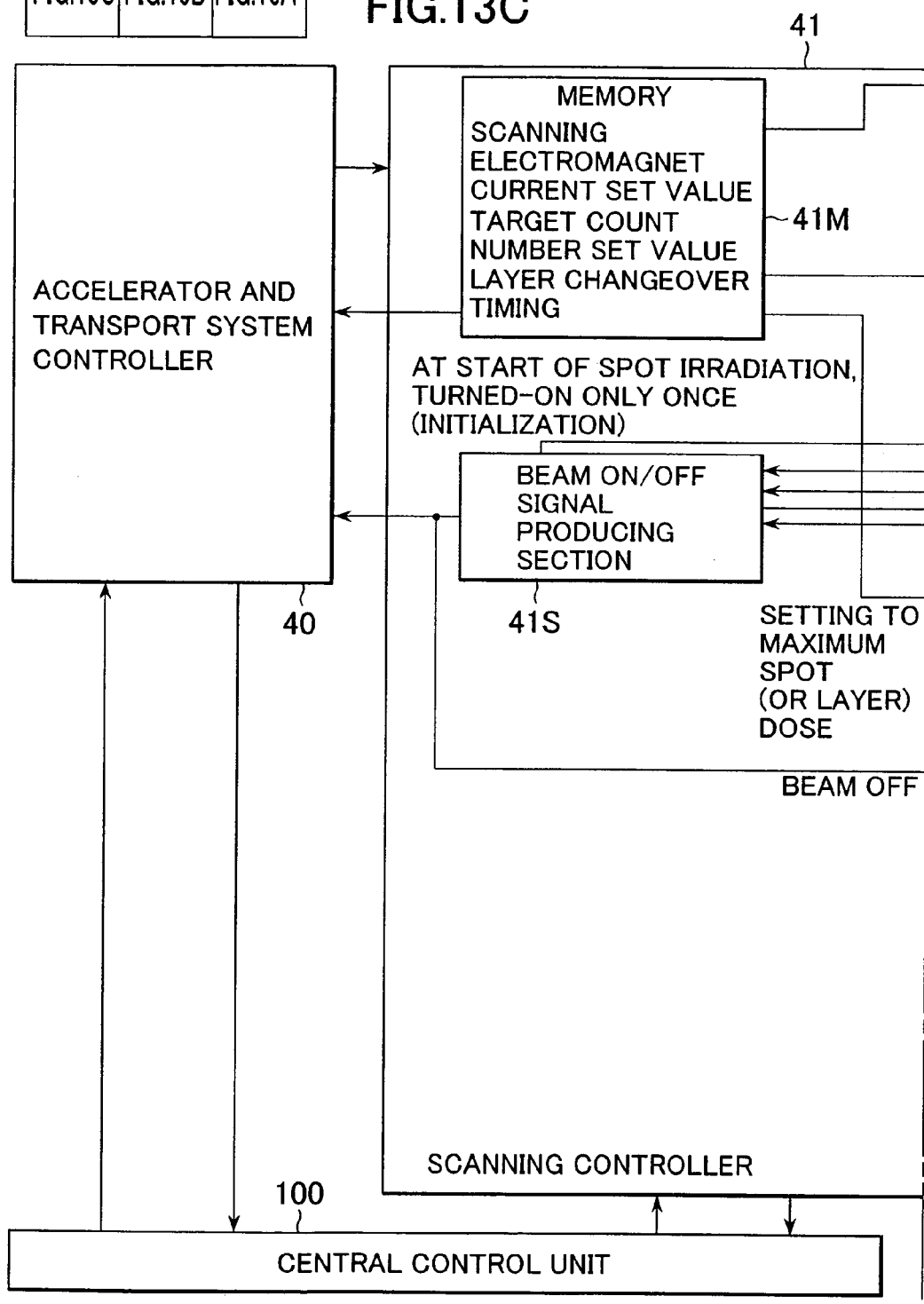

PARTICLE BEAM IRRADIATION APPARATUS, TREATMENT PLANNING UNIT, AND PARTICLE BEAM IRRADIATION METHOD

CROSS REFERENCE TO RELATED APPLICATIONS

The present application is a divisional of U.S. application Ser. No. 10/842,463, filed May 11, 2004, the disclosure of which is herewith incorporated by reference in its entirety.

BACKGROUND OF THE INVENTION

1. Field of the Invention

The present invention relates to a particle beam treatment system, and more particularly to a particle beam irradiation apparatus for treating an affected part by irradiating it with charged particle beams comprising proton ions, carbon ions, or the like, and a treatment planning unit using this particle beam irradiation apparatus, and a particle beam irradiation method.

2. Description of the Related Art

A treatment method for treating a patient with cancer or the like by irradiating the affected part of the patient with charged particle beams such as proton beams is known. The treatment system used for this treatment includes a charged particle beam generating unit, beam transport system, and treatment room. The charged particle beam accelerated by the accelerator of the charged particle beam generating unit reaches the beam delivery apparatusbeam delivery apparatus in the treatment room through the beam transport system, and after being scanned by scanning electromagnets provided in the beam delivery apparatusbeam delivery apparatus, the charged particle beam is applied from a nozzle to the affected part of the patient. A treatment method using such a treatment system is known that includes the steps of: stopping the output of the charged particle beam from the beam delivery apparatus; and in a state where the output of the charged particle beam is stopped, controlling the scanning electromagnets to change the irradiation position (spot) of the charged particle beam (so-called "scanning") and to start the output of the charged particle beam from the beam delivery apparatus after the aforementioned change (see, for example, European Patent Application No. 0779081A2 [FIG. 1 and the like]).

In the above-described conventional particle beam treatment system, in order to reduce to a minimum the exposure of normal tissue to radiation and perform a proper treatment with neither too much nor too little irradiation, the beam delivery apparatus has an irradiation dose monitor and/or beam position monitor for estimating the irradiation dose distribution, located at the downstream side of the electromagnets and immediately in front of a patient to be irradiated. In many cases, this monitor is of a type that accumulates charges ionized by the passage of beams in a capacitor, and that reads the voltage induced by the capacitor after spot irradiation. The capacity of this capacitor is determined so as to permit the amount of ionized charges by the spot subjected to a largest irradiation dose.

For the above-described capacitor, as the capacity decreases, the output voltage increases, thereby enhancing the resolution. Conversely, as the capacitor increases, the resolution decreases. Such being the situation, if the difference in irradiation dose between the spot subjected to the largest irradiation dose and that subjected to the smallest irradiation dose can be reduced, the capacity of the capacitor could be correspondingly reduced to enhance the resolution. This would effect the possibility of detecting more correctly an actual irradiation dose. However, the aforesaid conventional art does not particularly give consideration to the above-described reduction of the difference in irradiation dose, thus leaving room for improvement in the detection accuracy with respect to the actual irradiation dose.

Meanwhile, when performing irradiation to each spot, a target irradiation dose is set on a spot-by-spot basis. Once an integrated value of irradiation dose detected by the irradiation dose monitor has reached the target value, a beam stop command is outputted to the accelerator, and in response to it, the accelerator stops the output of a charged particle beam. With typical accelerator such as a slow cycling synchrotron or a cyclotron, even if the beam stop command is inputted as described above, strictly speaking, it is not impossible that some amount of response delay occurs rather than the output of the charged particle beam immediately stops. In such a case, even after the aforementioned target value was reached, the charged particle beam continues to be applied to the pertinent spot for the time period during the response delay time. This leaves room for improvement in the control accuracy with respect to the irradiation dose of the charged particle beam.

Since the irradiation dose monitor is an machine, it is difficult to perfectly eliminate the possibility that the irradiation dose monitor causes a malfunction or failure. Also, since the target irradiation dose for each spot is usually a value transmitted from a data base or a value calculated based on the transmitted value, it is not impossible that an improper value is inputted at the stage of the transmission or the calculation. However, the above-described conventional art does not particularly give consideration to such a monitor abnormality or an input error. This leaves room for improvement in the prevention of excessive irradiation of charged particle beams due to the aforementioned monitor abnormality or input error.

Furthermore, when performing irradiation to each spot, a target irradiation dose is set on a spot-by-spot basis. Once the integrated value of irradiation dose by the irradiation dose monitor has reached the target value, a beam stop command is outputted to the accelerator, and in response to it, the accelerator stops the output of the charged particle beam. Regarding such a beam stopping function, it is not impossible that equipment associated with this function causes a malfunction or failure, as well. However, the above-described conventional art does not particularly take a malfunction of such a beam stopping function into consideration. This leaves room for improvement in the prevention of excessive irradiation of charged particle beams due to the above-described malfunction or failure of the beam stopping function.

Accordingly, it is a first object of the present invention to provide a particle beam irradiation apparatus, treatment planning unit using this, and particle beam irradiation method that are capable of improving the detection accuracy with respect to an actual irradiation dose during treatment using charged particle beams.

It is a second object of the present invention to provide a particle beam irradiation apparatus and particle beam irradiation method that are capable of enhancing the control accuracy with respect to the irradiation dose of charged particle beams.

It is a third object of the present invention to provide a particle beam irradiation apparatus and particle beam irradiation method that are capable of reliably preventing the excessive irradiation of charged particle beams due to a monitor abnormality, input error, or the like.

It is a fourth object of the present invention to provide a particle beam irradiation apparatus and particle beam irradiation method that are capable of reliably preventing the excessive irradiation of charged particle beams due to a malfunction or the like of a beam stopping function.

It is a fifth object of the present invention to provide a particle beam irradiation apparatus and particle beam irradiation method that are capable of reducing the treatment time when performing irradiation of charged particle beams for each of a plurality of layer regions in a target.

SUMMARY OF THE INVENTION

To achieve the above-described first object, the present invention provides a particle beam irradiation apparatus that includes an accelerator for extracting a charged particle beam; an beam delivery apparatus having a charged particle beam scanning unit and outputting the charged particle beam extacted from the accelerator; and a controller that stops the output of the charged particle beam from the beam delivery apparatus, and that, in a state where the output of the charged particle beam is stopped, controls the charged particle beam scanning unit to change the irradiation position of the charged particle beam, start the output of the charged particle beam from the beam delivery apparatus after the above-described change, and perform irradiations of the charged particle beam with respect to at least one irradiation position a plurality of times based on treatment planning information.

In the present invention, the controller controls the charged particle beam scanning unit to perform irradiations of the charged particle beam with respect to at least one irradiation position a plurality of times. By virtue of this feature, regarding an irradiation position subjected to too much irradiation dose by one-time ion irradiation, it is possible to perform a divided irradiation so as to reduce an irradiation dose for each radiation. This allows the difference in irradiation dose between the irradiation position subjected to the largest dose and that subjected to the smallest dose to be reduced, thereby leveling off irradiation dose. As a result, the capacity of the capacitor of a position monitor can be correspondingly reduced to enhance the resolution, and therefore, the actual irradiation dose during treatment can be detected further correctly.

To achieve the above-described second object, the present invention provides a particle beam irradiation apparatus including a controller that controls the irradiation of the charged particle beam to the irradiation position so that the irradiation dose applied to the irradiation position becomes a set irradiation dose, in a state where the irradiation dose applied to the irradiation position during the time period from the outputting of a beam extraction stop signal at the time when the irradiation dose detected by the irradiation dose detector reaches the set irradiation dose up to the extraction stop of the charged particle beam from the accelerator, is added.

Even if the beam stop command is inputted, strictly speaking, it is not impossible that some amount of response delay occurs rather than the extraction of the charged particle beam from the accelerator immediately stops.

In the present invention, the controller can perform an irradiation of the charged particle beam to an irradiation position so that the irradiation dose at the irradiation position becomes a set irradiation dose, in a state where the irradiation dose applied to the irradiation position during the time period from the outputting of a beam extraction stop signal up to the extraction stop of the charged particle beam from the accelerator, is added. This allows the irradiation dose at each irradiation position to become substantially the set irradiation dose, thereby enabling the charged particle beam to be applied to each irradiation position with high accuracy. To control the irradiation dose, even if there is time delay between the outputting of the beam extraction stop signal and the extraction stop of the charged particle beam from the accelerator, the irradiation dose at each irradiation position can be made to be a set irradiation dose, allowing for the irradiation dose for the time period during the time delay. This makes it possible to irradiate, with high degree of accuracy, any irradiation position with charged particle beams of a dose substantially equal to the set irradiation dose.

To achieve the above-described third object, the present invention provides a particle beam irradiation apparatus including a controller that stops the output of the charged particle beam from the beam delivery apparatus, that, in a state where the output of the charged particle beam is stopped, controls the charged particle beam scanning unit to change the irradiation position of the charged particle beam and to start the output of the charged particle beam from the beam delivery apparatus after the above-described change, and that determines the occurrence of an abnormality based on an elapsed time from the irradiation start of the charged particle beam with respect to one irradiation position.

In the present invention, the controller determines the occurrence of an abnormality based on an elapsed time from the irradiation start of the charged particle beam with respect to one irradiation position. Therefore, even if the irradiation time of the charged particle beam is likely to abnormally elongate due to the occurrence of a malfunction or failure of the irradiation dose detector, or an improper input value, the irradiation of the charged particle beam can be stopped after a certain time has elapsed. This reliably prevents an excessive irradiation to a target, and further improves the safety.

To achieve the above-described fourth object, the present invention provides a particle beam irradiation apparatus including a controller that stops the output of the charged particle beam from the beam delivery apparatus, that, in a state where the output of the charged particle beam is stopped, controls the charged particle beam scanning unit to change the irradiation position of the charged particle beam and to start the output of the charged particle beam from the beam delivery apparatus after the above-described change, and that determines the occurrence of an abnormality using the irradiation dose detected by the irradiation detector and a second set irradiation dose larger than respective first set irradiation doses with respect to a plurality of irradiation positions in the target.

In the present invention, the controller determines the occurrence of an abnormality, using the irradiation dose detected by the irradiation dose detector and the second set dose larger than respective first set doses with respect to a plurality of irradiation positions in the target. Therefore, even if, due to a malfunction or the like of the beam stopping function, the charged particle beam does not readily stop and the irradiation dose is likely to abnormally increase, the irradiation can be stopped at a certain upper limit irradiation dose, thereby reliably preventing an excessive irradiation to the target. This further enhances the safety.

To achieve the above-described fifth object, the present invention provides a particle beam irradiation apparatus including a controller that performs control to decelerate the charged particle beam in the accelerator when the irradiation of the charged particle beam with respect to one of a plurality of layer regions that are different in irradiation energy from each other in a target to be irradiated with the charged particle beam from the beam delivery apparatus, has been completed.

In the spot scanning irradiation according to the present invention, as the size of a target changes, the number of spots in a layer changes, and consequently, the time required to complete an irradiation to all spots in the layer changes. Regarding the allowable extraction period of the synchrotron, if it is set to be long with a large target assumed, the irradiations to all layers takes much time to complete, thereby elongating the treatment time for a patient. In the present invention, after the irradiation in a layer region has been completed, the charged particle beam in the accelerator is decelerated, and therefore, the allowable extraction period of the charged particle beams in the accelerator can be earlier terminated. As a result, even when it is necessary to irradiate a plurality of layer regions with charged particle beams, the treatment time can be made short.

BRIEF DESCRIPTION OF THE DRAWINGS

FIG. 7 is a table showing an example of the number of times of division of each layer at the time of irradiation, the number of times of division being planned in the treatment planning unit shown in FIG. 1;

FIG. 8 is a table showing an example of division mode of each layer at the time of irradiation, the division mode being planned in the treatment planning unit shown in FIG. 1;

FIG. 11 is a table showing the contents of command signals to execute the scanning mode of each layer at the time of irradiation, the command signal having been planned in the treatment planning unit shown in FIG. 1;

FIG. 13 is a detailed functional block diagram of the functional construction of the scanning controller shown in FIG. 1;

DESCRIPTION OF THE PREFERRED EMBODIMENTS

Hereinafter, a particle beam treatment system having a particle beam irradiation apparatus according to an embodiment of the present invention will be described with reference to the accompanying drawings.

Figure 1:
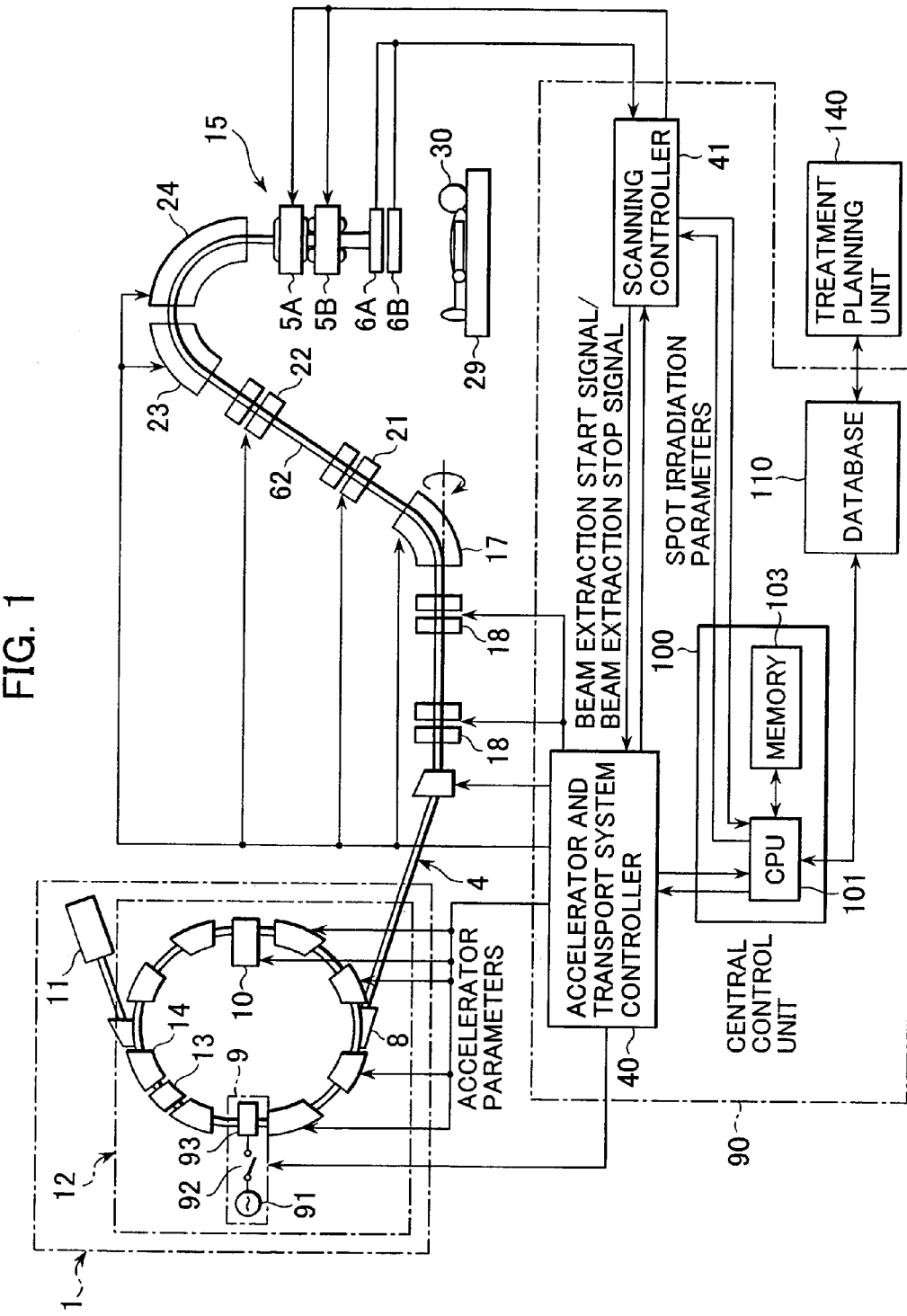
FIG. 1 is a schematic diagram of the overall construction of a particle beam irradiation apparatus according to an embodiment of the present invention.

As shown in FIG. 1, a proton beam treatment system, which is a particle beam treatment system according to this embodiment, includes a charged particle beam generating unit 1 and a beam transport system 4 connected to the downstream side of the charged particle beam generating unit 1.

The charged particle beam generating unit 1 comprises an ion source (not shown), a pre-stage charged particle beam generating unit (linear accelerator (linac)) 11, and a synchrotron (accelerator) 12. The synchrotron 12 includes a high-frequency applying unit 9 and acceleration unit 10. The high-frequency applying unit 9 is constructed by connecting a high-frequency applying electrode 93 disposed on the circulating orbit of the synchrotron 12 and a high-frequency power source 91 by an open/close switch 92. The acceleration unit (second element; charged particle beam energy changing unit) 10 comprises a high-frequency accelerating cavity (not shown) disposed on the circulating orbit thereof, and a high-frequency power source (not shown) for applying a high-frequency power to the high-frequency accelerating cavity. Ions generated in the ion source, e.g., hydrogen ions (protons) or carbon ions, are accelerated by the pre-stage charged particle beam generating unit (e.g., linear charged particle beam generating unit) 11. The ion beam (proton beam) emitted from the pre-stage charged particle beam generating unit 11 is injected into the synchrotron 12. In the synchrotron 12, this ion beam, which is a charged particle beam, is given energy and accelerated by the high-frequency power that is applied to the ion beam through the high-frequency accelerating cavity from the high-frequency power source 91. After the energy of the ion beam circulating through the synchrotron 12 has been increased up to a set energy (e.g., 100 to 200 MeV), a high frequency for emission from the high-frequency power source 91 reaches the high-frequency applying electrode 93 through the open/close switch 92 in a closed state, and is applied to the ion beam from the high-frequency applying electrode 93. The application of this high-frequency causes the ion beam that is circulating within a stability limit to shift to the outside of the stability limit, thereby extracting the ion beam from the synchrotron 12 through an extraction deflector 8. At the extraction of the ion beam, currents supplied to quadrupole electromagnets 13 and bending electromagnets 14 are held at set values, and the stability limit is held substantially constant. Opening the open/close switch 92 to stop the application of the high frequency power to the high-frequency applying electrode 93, stops the extraction of the ion beam from the synchrotron 12.

The ion beam extracted from the synchrotron 12 is transported to the downstream side of the beam transport system 4. The beam transport system 4 includes quadrupole electromagnets 18 and a deflection electromagnet 17; and quadrupole electromagnets 21 and 22, and deflection electromagnets 23 and 24 that are sequentially arranged on a beam path 62 communicating with the beam delivery apparatus 15 provided in a treatment room from the upstream side toward the beam traveling direction. Here, the aforementioned electromagnets each constitute a first element. The ion beam introduced into the beam transport system 4 is transported to the beam delivery apparatus 15 through the beam path 62.

The treatment room has the beam delivery apparatus 15 affixed to a rotating gantry (not shown) provided therein. A beam transport unit having an inverse U-shape and including a part of the beam path 62 in the beam transport system 4, and the beam delivery apparatus 15 are disposed in a rotating drum (not shown) with a substantially cylindrical shape, of the rotating gantry (not shown). The rotating drum is configured so as to be rotated by a motor (not shown). A treatment gauge (not shown) is formed in the rotating drum.

The beam delivery apparatus 15 has a casing (not shown) affixed to the rotating drum and connected to the aforementioned inverse U-shaped beam transport unit. Scanning electromagnets 5A and 5B for scanning a beam, a dose monitor 6A, a position monitor 6B and the like are disposed in the casing. The scanning electromagnets 5A and 5B are used for deflecting a beam, for example, in directions orthogonally intersecting each other (an X-direction and Y-direction) on a plane perpendicular to the beam axis, and moving an irradiation position in the X-direction and Y-direction.

Before an ion beam is applied from the beam delivery apparatus 15, a bed 29 for treatment is moved by a bed drive unit (not shown) and inserted into the aforementioned treatment gauge, and the positioning of the bed 29 for irradiation with respect to the beam delivery apparatus 15 is performed. The rotating drum is rotated by controlling the rotation of the motor by a gantry controller (not shown) so that the beam axis of the beam delivery apparatus 15 turns toward the affected part of a patient 30. The ion beam introduced into the beam delivery apparatus 15 from the inverse U-shaped beam transport unit through the beam path 62 is caused to sequentially scan irradiation positions by the scanning electromagnets (charged particle beam scanning unit) 5A and 5B, and applied to the affected part (e.g., occurrence region of cancer or tumor) of the patient 30. This ion beam releases its energy in the affected part, and forms a high dose region there. The scanning electromagnets 5A and 5B in the beam delivery apparatus 15 are controlled by a scanning controller 41 disposed, for example, in the gantry chamber in a treatment unit.

A control system included in the proton beam treatment system according to this embodiment will be described with reference to FIG. 1. This control system 90 comprises a central control unit 100, storage unit 110 storing treatment planning database, scanning controller 41, and accelerator and transport system controller 40 (hereinafter referred to as an "accelerator controller"). Furthermore, the proton beam treatment system according to this embodiment has a treatment planning unit 140.

While the aforementioned treatment planning data (patient data) stored in the storage unit 110 on a patient-by-patient basis is not particularly shown, the treatment planning data includes data such as patient ID numbers, irradiation doses (throgh a treatment and/or per fraction), irradiation energy, irradiation directions, irradiation positions, and others.

The central control unit 100 has a CPU and memory 103. The CPU 100 reads the above-described treatment planning data concerning patients to be treated from the storage unit 110, using the inputted patient identification information. The control pattern with respect to the exciting power supply to each of the above-described electromagnets is determined by the value of irradiation energy out of the treatment planning data on a patient-by-patient basis.

The memory 103 stores a power supply control table in advance. Specifically, for example, in accordance with various values of irradiation energy (70, 80, 90, . . . [MeV]), values of supply exciting power or their patterns with respect to a quadrupole electromagnet 13 and deflection electromagnet 14 in the charged particle beam generating unit 1 including the synchrotron 12; and the quadrupole electromagnets 18, deflection electromagnet 17, the quadrupole electromagnets 21 and 22, and deflection electromagnets 23 and 24 in the beam transport system 4, are preset.

Also, using the above-described treatment planning data and power supply control table, the CPU 101 as a control information producing unit, produces control command data (control command information) for controlling the electromagnets provided on the charged particle beam generating unit 1 and the beam paths, regarding a patient to be treated. Then, the CPU 101 outputs the control command data produced in this manner to the scanning controller 41 and accelerator controller 40.

One of the features of this embodiment lies in that, based on the treatment planning data created by the treatment planning unit 140, the central control unit 100, scanning controller 41, and accelerator controller 40 performs control operations in close liaison with one another as follows: (1) they stops the output of an ion beam from the beam delivery apparatus 150, and in a state where the output of the ion beam is stopped, they control the scanning electromagnets 5A and 5B to change the irradiation position (spot) of the ion beam and to start the output of the ion beam from the beam delivery apparatus 15 after the aforementioned change (so-called "scanning"); (2) in order to reduce variations in irradiation dose at a spot, they control the synchrotron 12 and beam delivery apparatus 15 to divide an irradiation of an ion beam with respect to at least one identical irradiation position (spot) at which the dose otherwise would exceed a division reference irradiation dose (discussed below), into a plurality of times of irradiations.

Hereinafter, detailed explanation thereof will be provided with reference to FIGS. 2 to 18.

First, the creation of a treatment plan by the treatment planning unit 140 is explained. The treatment planning unit 140 is, for example, constituted of a personal computer. While its illustration is omitted, the treatment planning unit 140 includes an input unit (e.g., keyboard) which can be operated by an operator and with which the operator can input; a computing unit (e.g., CPU) that performs a predetermined arithmetic processing based on an input result by the aforementioned input means and operation means; an input/output interface that performs the input/output of information, such as the input of external image data and the output of treatment planning data created by this computing unit; and a display unit.

Figure 2:
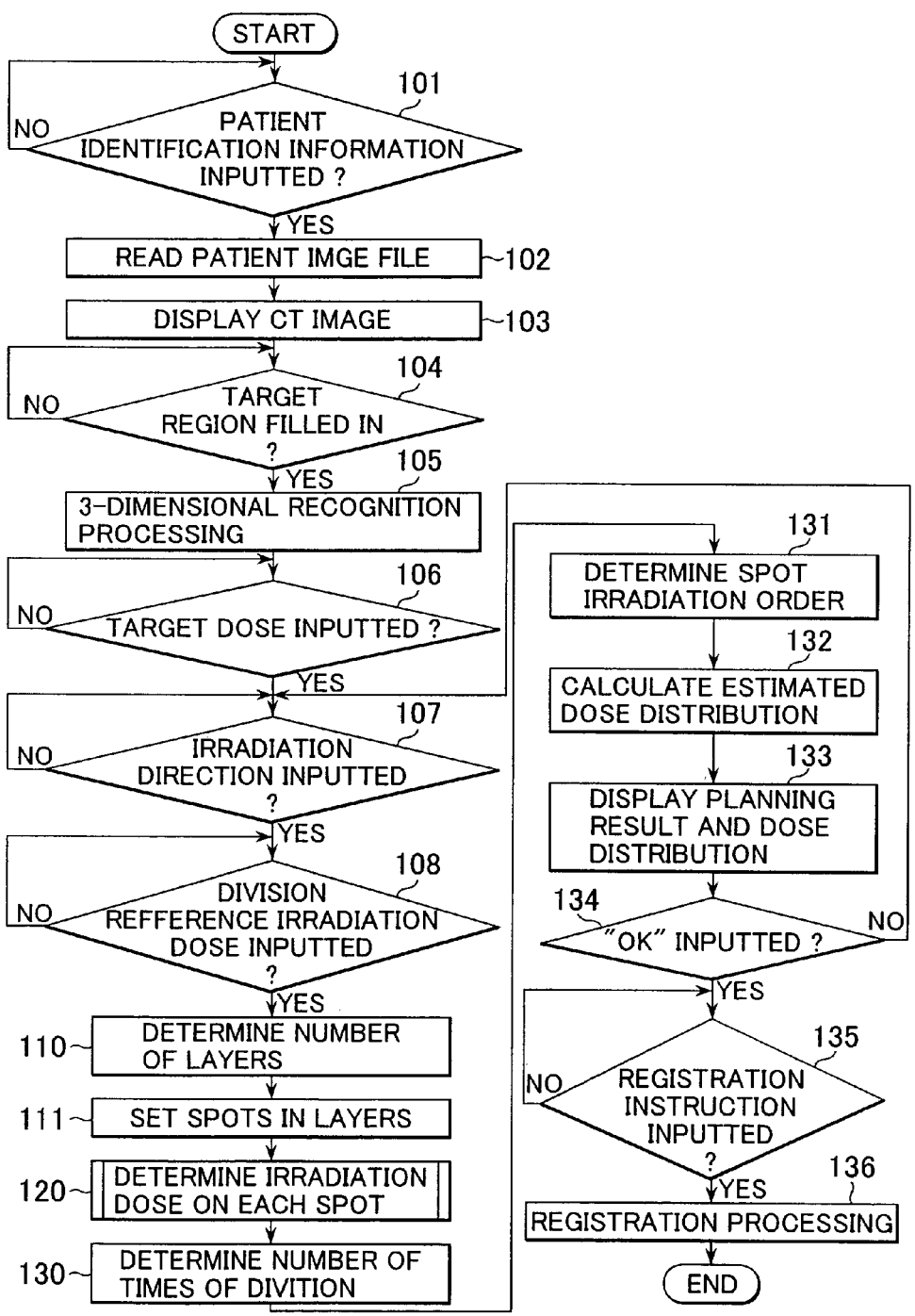
FIG. 2 is a flowchart showing the control procedure executed by the computing means of the treatment planning unit shown in FIG. 1.

FIG. 2 is a flowchart showing arithmetic processing steps executed by the aforementioned computing means of the treatment planning unit 140. In FIG. 2, if an operator (usually a doctor or medical staff) inputs identification information (e.g., a name, ID number) about a patient to be treated via the input unit, the determination in step 101 is satisfied, and the processing advances to step 102, where a patient image file (file previously taken by extra imaging means such as CT scanner and stored in the database of the storage unit 110) of a pertinent patient is read. Here, the patient image file is tomography image information.

Thereafter, in step 103, the read patient image file is outputted on a display unit as display signals, and a corresponding display is made. If the operator performs specification by filling in a target region to be irradiated with an ion beam via the input unit while watching the displayed patient image file, the determination in step 104 is satisfied, and the processing advances to step 105, where recognition processing is three-dimensionally performed regarding the filled-in region.

In this situation, if the operator inputs a target dose to be applied to a corresponding target region via the input unit, the determination in step 106 is satisfied. Furthermore, if the operator inputs an irradiation direction of the ion beam, the determination in step 107 is satisfied, and the processing advances to step 108. Moreover, if the operator inputs, via the input unit, a division reference irradiation dose, which is a reference irradiation dose such that a divided irradiation is to be performed if an irradiation dose per unit spot exceeds this reference irradiation dose, the determination in step 108 is satisfied, and the processing advances to step 110.

Figure 3:
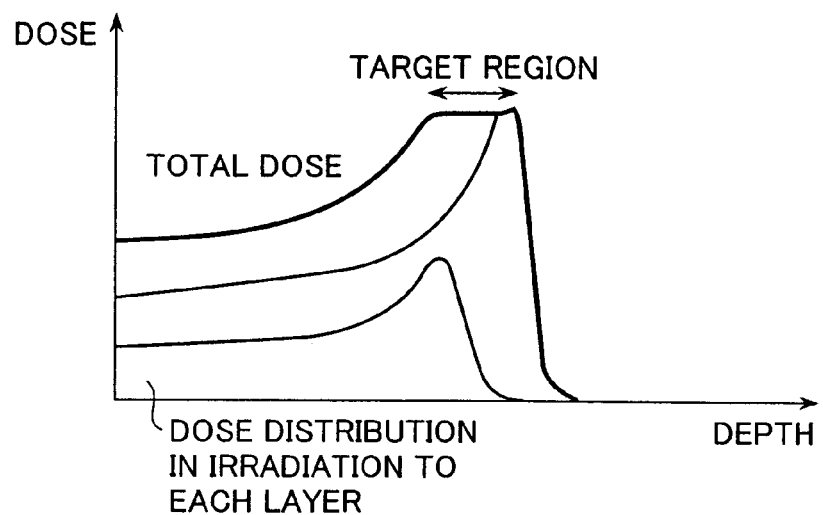
FIG. 3 is a schematic diagram showing an example of distribution of dose applied to each layer in order to secure uniformity in an affected area.

Here, description will be made of the relationship between the depth of a target and energy of an ion beam. The target is a region, including an affected part, to be irradiated with an ion beam, and is somewhat larger than the affected part. FIG. 3 shows the relationship between the depth of the target in a body and the irradiation dose of ion beam. The peak of dose as shown in FIG. 3 is referred to as a "Bragg peak". The application of an ion beam to the target is performed in the position of the Bragg peak. The position of Bragg peak varies depending on the energy of ion beam. Therefore, dividing the target into a plurality of layers (slices) in the depth direction (traveling direction of ion beam in the body), and changing the energy of ion beam to the energy in correspondence with a depth (a layer) allows the ion beam to be irradiated throughout the entire target (target region) having a thickness in the depth direction as uniformly as possible. From this point of view, in step 110, the number of layers in the target region to be divided in the depth direction is determined. One possible determination method for determining the number of layers is to set the thickness of a layer, and to automatically determine the number of layers in accordance with the aforementioned thickness and a thickness of the target region in the depth direction. The thickness of layer may be a fixed value irrespective of the size of the target region, or alternatively may be automatically determined appropriately to the maximum depth of the target region. Still alternatively, the thickness of layer may be automatically determined in accordance with the spread of the energy of ion beam, or simply, the number itself of layers may be inputted by the operator via the input unit instead of determining the thickness of layer.

Figure 4:
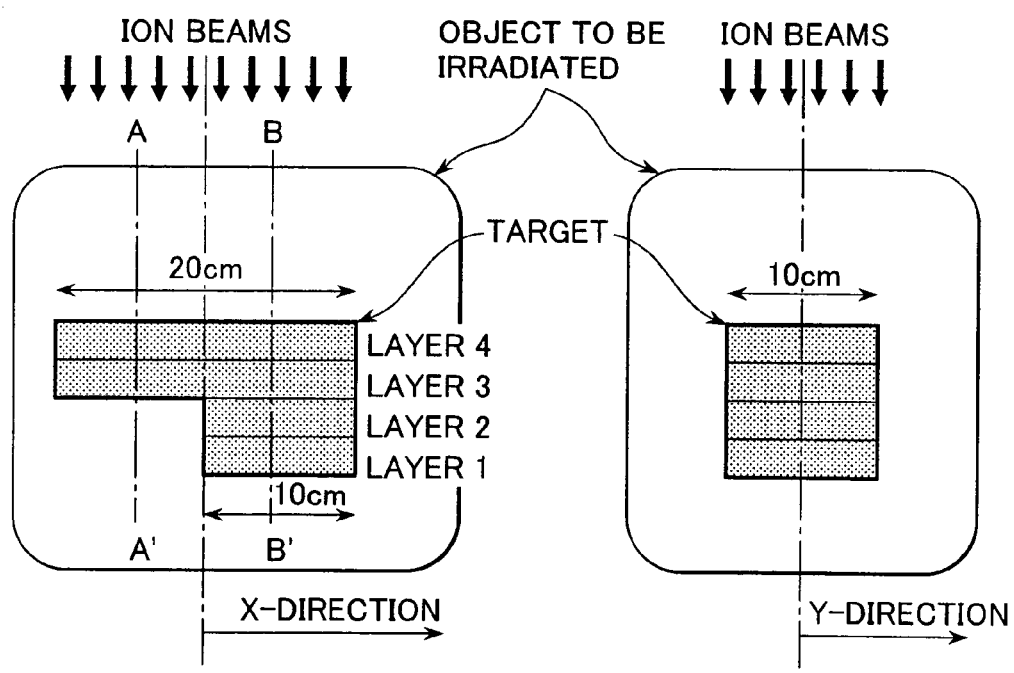
FIG. 4 is a diagram illustrating an example of affected area to be irradiated by the particle beam irradiatoin apparatus shown in FIG. 1.
Figure 5:
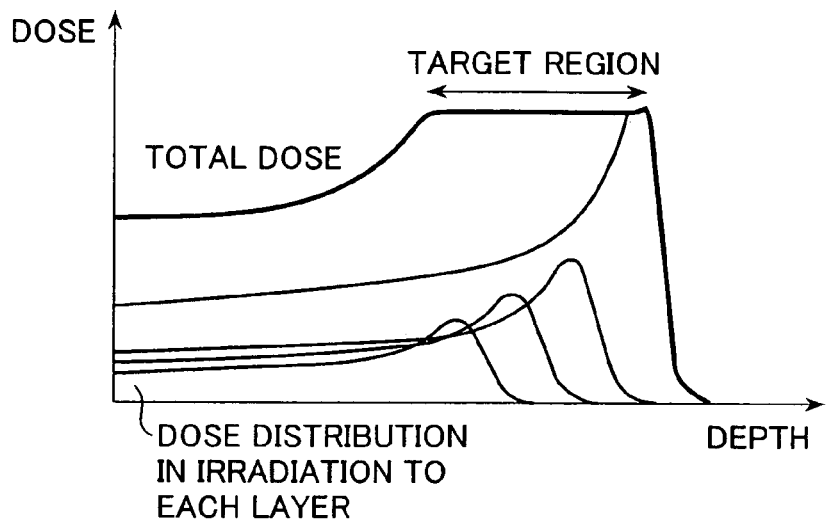
FIG. 5 is a schematic diagram showing an example of distribution of the dose applied to each layer in order to secure uniformity in an affected area.

FIG. 4 is a diagram showing an example of layers determined in the above-described manner. In this example, the number of layers is four: layers 1, 2, 3, and 4 in this order from the lowest layer. The layers 1 and 2 each have a spread of 10 cm in the X-direction and a spread of 10 cm in the Y-direction. The layers 3 and 4 each have a spread of 20 cm in the X-direction and a spread of 10 cm in the Y-direction. FIG. 3 represents an example of dose distribution in the depth direction as viewed from the line A–A' in FIG. 4. On the other hand, FIG. 5 represents an example of dose distribution in the depth direction as viewed from the line B–B' in FIG. 4.

After the number of layers has been determined in this manner, the proceeding advances to step 111, where the number (and positions) of spots that divide each layer (target cross section) in the direction perpendicular to the depth direction, is determined. On this determination, like the above-described layers, one spot diameter is set, and the number of spots is automatically determined in accordance with the size of the spot and the size of the pertinent layer. The spot diameter may be a fixed value, or alternatively may be automatically determined appropriately to the target cross section. Still alternatively, the spot diameter may be automatically determined appropriately to the size of ion beam (i.e., the beam diameter), or simply, spot positions themselves or the distances themselves between spot positions may be inputted by the operator via the input unit instead of determining the spot size. After step 111 has been completed, the processing advances to step 120, where the irradiation dose at each spot in all layers is determined.

Figure 6:
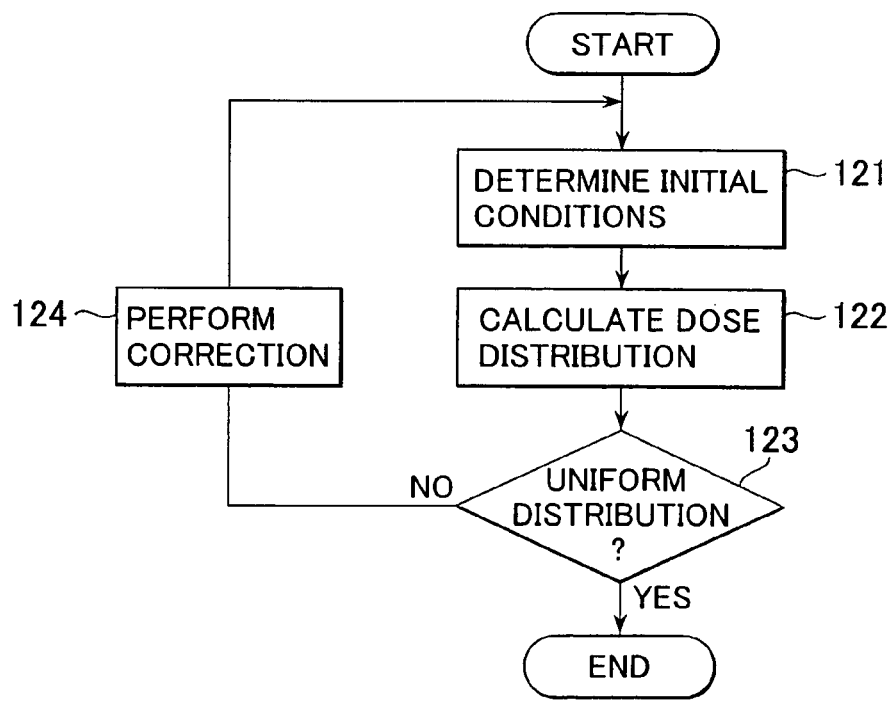
FIG. 6 is a flowchart showing the control procedure executed by the computing means of the treatment planning unit shown in FIG. 1.

FIG. 6 is a flowchart showing detailed procedure in the aforementioned step 120. As described above, basically, the application of an ion beam to the target is performed in the position of the Bragg peak, and it is desirable that the ion beam be irradiated throughout the entire target (target region) having a thickness in the depth direction as uniformly as possible. On the determination in the irradiation dose at each spot, therefore, it is necessary to ultimately secure a uniform irradiation throughout the entire target region. In light of the above, in steps 121–123, firstly initial condition are determined in step 121. Specifically, by the accumulation of past calculation examples, the utilization of simple models or the like, the irradiation doses with respect to all spots on layer-by-layer basis that are deemed to correspond to the target doses, the irradiation direction of ion beam, and the numbers of layers that were inputted or determined in steps 106 to 111, are determined as temporary values.

Thereafter, the processing advances to step 122, where, using a known method, a simulation calculation is performed as to how the actual dose distribution in the entire target region becomes, if an irradiation is performed using the values of irradiation doses with respect to all spots, the doses having been determined in step 121. Then, in step 123, it is determined whether the aforementioned calculated dose distribution is uniform throughout substantially the entire region of the target, namely, whether variations remain within a given limit. If not so, the processing advances to step 124, where a predetermined correction is made. This correction may be such that the irradiation doses at spots somewhat outstandingly higher/lower than an average dose value are automatically lowered/raised with a correction width, and that the correction width may be set by a manual operation. After such a correction, the processing returns to step 121 and the same procedure is repeated. Therefore, the correction in step 124 and the dose distribution calculation in step 122 are performed until the irradiation dose distribution becomes uniform to a certain extent. Thus, ultimately, the irradiation doses with respect all spots that allow substantially uniform dose distribution to be implemented in the entire target region, are determined. Thereafter, the processing advances to step 130.

In this stage, although the irradiation doses to all spots have each been determined, each of all these spots is set to be irradiated with a pertinent allocated irradiation dose at one time. In step 130, if there are any irradiation doses exceeding the division reference irradiation dose inputted before in step 108, out of the irradiation doses determined with respect to all spots, the ion beam irradiation to each of such spots is not performed at one time, but is performed in the form of irradiations divided into a plurality of times (at least two times). Here, we assume the number N of irradiations to be a minimum natural number n that satisfies the relationship: $n \geq R/Rs$, where R and Rs, respectively, denote the irradiation dose and the division reference irradiation dose at a pertinent spot. In other words, the number N of irradiations is assumed to be a value obtained by rounding-up the decimal places of R divided by Rs. Therefore, if N=1, then $R \leq Rs$, and hence a plurality of times of divided irradiations are not performed (namely, the irradiation is performed at one time). If N=2, then R>Rs, and hence it is planned that irradiations divided into a plurality of times are performed.

FIG. 7 shows an example (layers 1 to 4) of divided irradiations as described above with reference to FIGS. 4 and 5. In this example, the division reference dose is assumed to be 10 (a relative value without unit; the same shall apply hereinafter). As shown in FIG. 7, regarding the layer 1, before division processing (i.e., when the irradiation is performed at one time), the irradiation dose at each spot was 70. Such being the situation, it is planned that irradiations divided into seven times are performed, the irradiation dose for each divided irradiation being 10. Likewise, regarding the layers 2, 3, and 4, the irradiation doses at each spot before division processing were 25, 17.9, and 12.6, respectively. Accordingly, in the layers 2, 3, and 4, respectively, it is planned that irradiations divided into three, two, and two times were performed, the irradiation dose for each divided irradiation being 8.3, 9, and 6.3, respectively.

More specific explanations of the above will be provided with reference to FIG. 8. As described above, regarding the layer 1 (the region corresponding to the right half of the layer 1 shown in FIG. 8; here, the right-left direction in FIG. 8 corresponds to that in FIG. 4), irradiations divided into seven times are performed, and it is planned that an irradiation with irradiation dose of 10 is repeated in each of the first-time to seventh-time irradiations. Regarding the layer 2 (the region corresponding to the right half of the layer 2 shown in FIG. 8), it is planned that an irradiation with irradiation dose of 8.3 is repeated three times. Regarding the layer 3, with respect to the region shown in the right half in FIG. 8, it is planned that an irradiation with irradiation dose of 9.0 is repeated two times, while with respect to the region shown in the left half in FIG. 8, it is planned that an irradiation with irradiation dose of 10 is repeated seven times. Regarding the layer 4, with respect to the region shown in the right half in FIG. 8, it is planned that an irradiation with an irradiation dose of 6.3 is repeated two times, while with respect to the region shown in the left half in FIG. 8, it is planned that an irradiation with irradiation dose of 8.3 is repeated three times.

After step 130 has been completed, the processing advances to step 131, where the order of the irradiation with respect to spots in each of the layers is determined. Specifically, in the proton beam treatment system according to this embodiment, as described above, the output of an ion beam from the beam delivery apparatus 15 is stopped, and in the state the output of the ion beam is stopped, a scanning irradiation to change the irradiation position (spot) is performed. In step 131, it is determined how the ion beam is to be moved with respect to each spot in the scanning irradiation. Here, the ion beam to be applied to the target is narrow, and its diameter is a little larger than that of the spot diameter.

Figure 9:
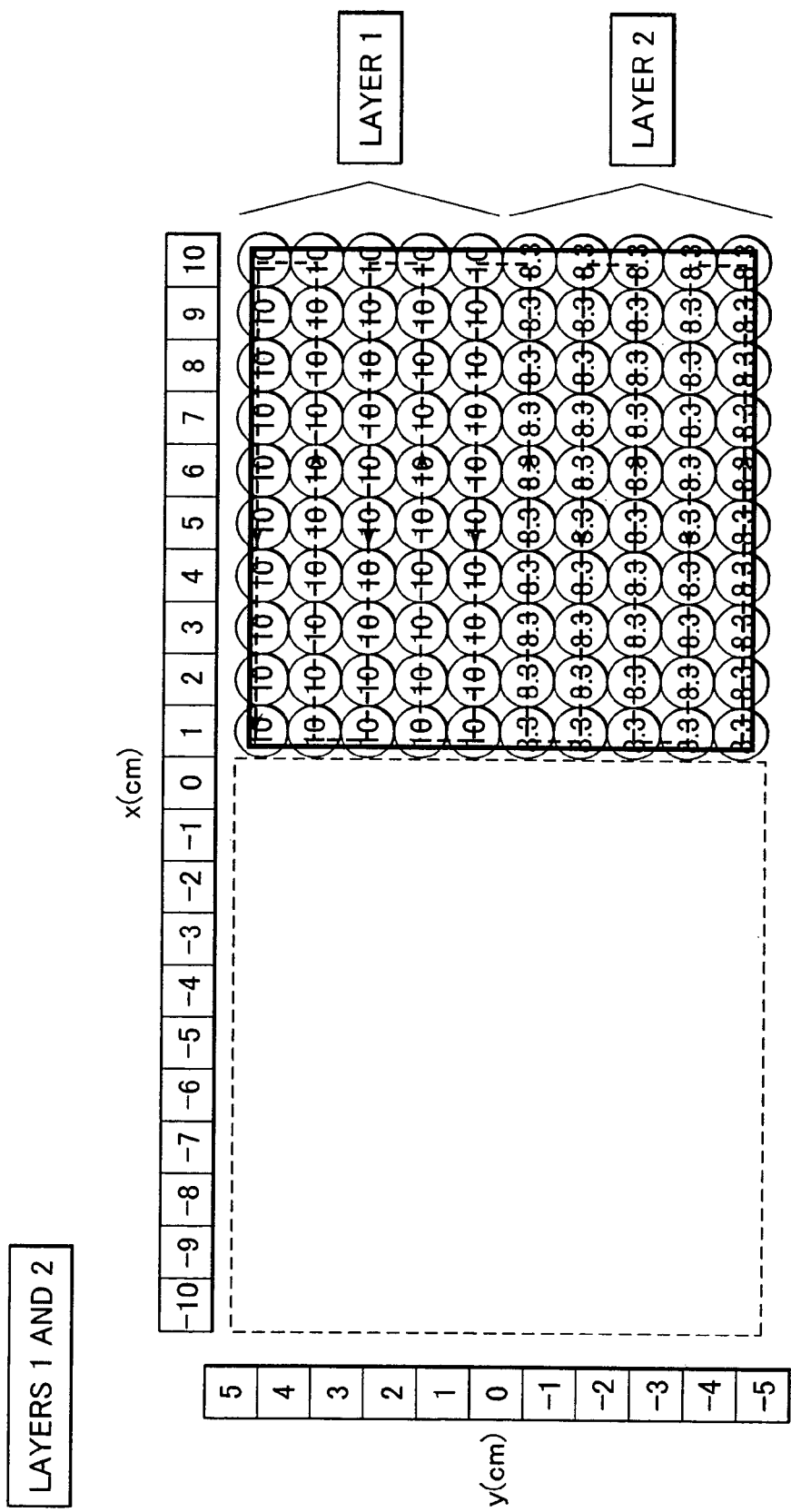
FIG. 9 is a schematic plan view illustrating an example of scanning mode of each layer at the time of irradiation, the scanning mode having been planned in the treatment planning unit shown in FIG. 1.
Figure 10:
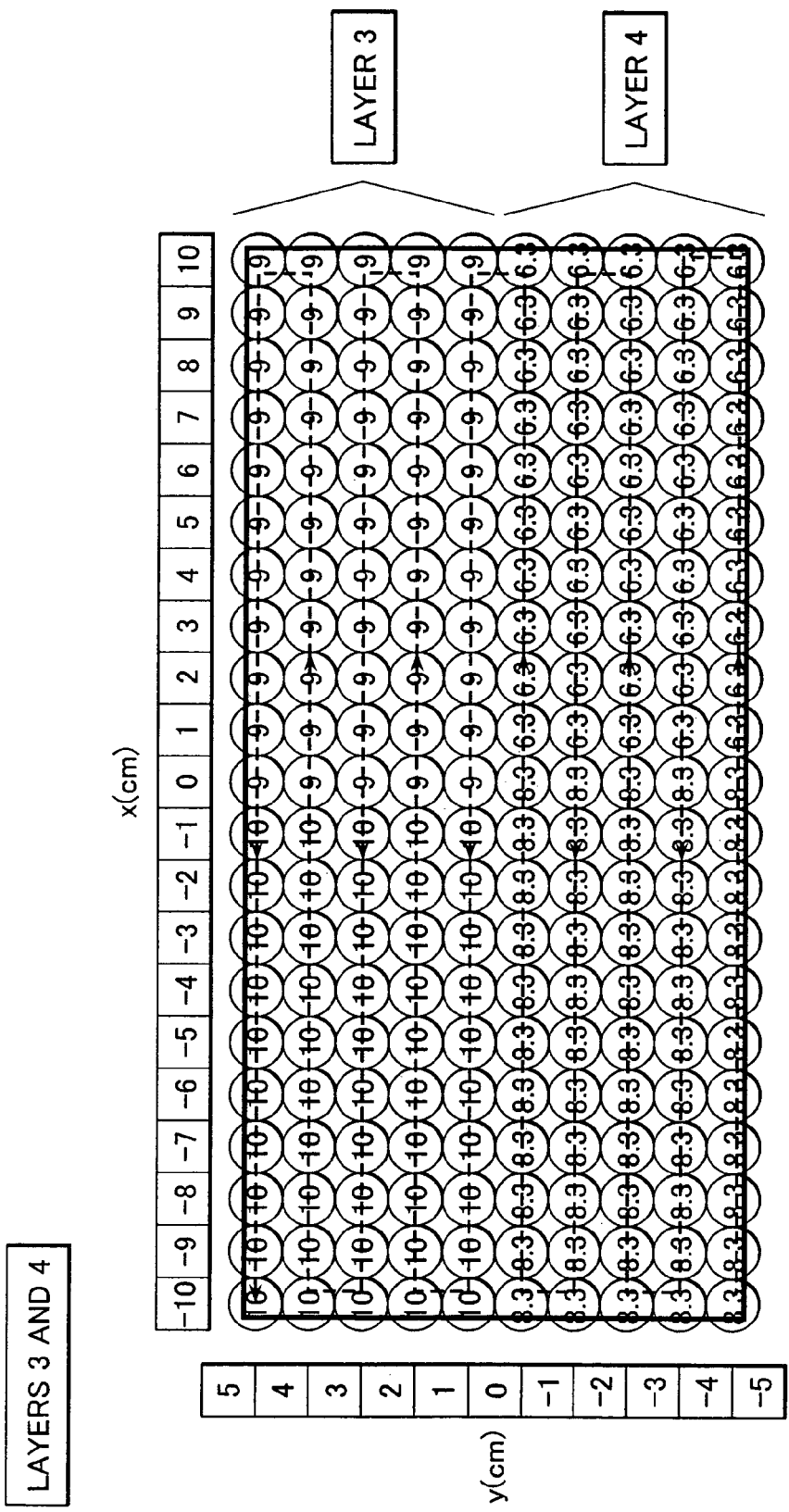
FIG. 10 is a schematic plan view illustrating another example of scanning mode of each layer at the time of irradiation, the scanning mode having been planned in the treatment planning unit shown in FIG. 1.

FIGS. 9 and 10 each show an example of the setting of the order of spot irradiation. This order of spot irradiation order corresponds to the example described with reference to FIGS. 4, 3, 5, 7, and 8.

FIG. 9 shows the setting of irradiation orders in both the layers 1 and 2 in a combined and simplified manner. As shown in FIG. 9, for each of the layers 1 and 2, 100 spots in total are set in a lattice shape of 10 rows and 10 columns. The application of an ion beam to the target (the square region in FIG. 9) of the layers 1 and 2 is performed, for example, in a manner as follows: an irradiation is performed on a spot-by-spot basis from one end (the left lower corner in FIG. 9) in the spot row (including ten spots) situated at one end of these layers toward the other end (the right lower corner in FIG. 9) of this spot row, i.e., from the left toward the right in FIG. 9. After the irradiation to the other end has been completed, the irradiation is performed on a spot-by-spot basis from one end (the right lower end in FIG. 9) in another spot row adjacent to the aforementioned spot row toward the other end (the left end in FIG. 9) of the other row, i.e., from the right toward the left in FIG. 9. After the irradiation to the other end in the other row has been completed, the ion beam moves to a next other spot row adjacent. In this manner, in this embodiment, it is planned that, in the horizontal surface of each of the layers 1 and 2, the ion beam is moved by inversing its traveling direction (i.e., by causing the ion beam to meander) for each of the adjacent spot rows, until the ion beam reaches the last spot (the left upper corner in FIG. 9) in the last spot row, thus completing an irradiation operation (one of a plurality of times of scanning operations) with respect to the layers 1 and 2. Regarding the layer 1, the irradiation dose at each of the total of 100 spots is 10 for each divided irradiation, and as described above, one meandering scanning operation for each of the spot rows is repeated seven times. From the first-time through seventh-time scanning operations, the same irradiation order setting may be applied. Alternatively, however, in order to speed up an irradiation, for example, the second-time scanning may be performed from the left upper corner toward the left lower corner in FIG. 9 along the reverse route (the same shall apply hereinafter). Also, regarding the layer 2, as described with reference to FIG. 8, it is planned that the irradiation dose at each of the total of 100 spots is 8.3 for each divided irradiation, and it is planned that one meandering scanning operation as described above is repeated three times.

FIG. 10 shows the setting of irradiation orders in both the layers 3 and 4 in a combined and simplified manner, although this is an example of the first-time and second-time scanning operations. As shown in FIG. 10, for each of the layers 1 and 2, 200 spots in total are set in a lattice shape of 10 rows and 20 columns. The application of an ion beam to the target (the rectangular region in FIG. 9) of the layers 3 and 4 is performed, as is the case with the layers 1 and 2, for example, in a manner as follows: an irradiation is performed on a spot-by-spot basis from one end (the left lower corner in FIG. 10) in the spot row (including twenty spots) situated at one end of these layers toward another end (the right lower corner in FIG. 10) in this spot row. After the irradiation to the other end has been completed, the irradiation is performed from one end (the right lower end in FIG. 10) in another spot row adjacent to the aforementioned spot row toward the other end (the left end in FIG. 10) of the other row. After the irradiation to the other end in the other row has been completed, the ion beam moves to a next other spot row adjacent. In this way, in this embodiment, also for each of the layers 3 and 4, it is planned that, in the horizontal surface, the ion beam is moved by causing the ion beam to meander for each of the adjacent spot rows, and that one irradiation operation (one of two scanning operations) with respect to the layers 3 and 4 is completed.

In the layer 3, as shown in FIG. 8, the irradiation dose for each divided irradiation with respect to each of the total of 200 spots is 9 for each of the 100 spots in the right half region in FIGS. 10, and 10 for each of the 100 spots in the left half region in FIG. 10. It is planned, therefore, that one scanning operation that meanders for each of the spot rows while changing an irradiation dose at a midpoint in a spot row, is repeated two times. Likewise, in the layer 4, the irradiation dose for each divided irradiation with respect of each of the total of 200 spots is 6.3 for each of the 100 spots in the right half region in FIG. 10, and 8.3 for each of the 100 spots in the right half region in FIG. 10. It is planned, therefore, that one scanning operation that meanders for each of the spot rows while changing an irradiation dose at a midpoint in a spot row, is repeated two times.

Regarding each of the layers 3 and 4, in irradiations at the third time and afterward, the irradiation to the 100 spots in the right half in FIG. 10 do not need, and the irradiation to the 100 spots in the left half alone is performed (see FIG. 8). Regarding the irradiation order then, although it is not particularly illustrated, for example, performing like the layers 1 and 2 shown in FIG. 9 suffices for the layers 3 and 4. Regarding the layer 3, the irradiation dose with respect of each of its 100 spots is 10 for each divided irradiation, and it is planned that in the left half region alone, for example, one meandering scanning operation is performed five times (in the third-time to seventh-time scanning operations). Likewise, in the layer 4, the irradiation dose with respect of each of its 100 spots is 8.3 for each divided irradiation, and it is planned that in the left half region alone, for example, one meandering scanning operation is performed (in the third-time scanning).

After the spot irradiation order has been determined as described above, the processing advances to step 132, where the dose distribution at a target area that is estimated when irradiations are performed with the irradiation dose with respect to all layers and all spots and in the spot irradiation order that were each determined as described above, is calculated using a known method. This simulation uses a method with higher accuracy and requiring a little longer calculation time than a simplified method as shown before in FIG. 6. Hereafter, the processing advances to step 133, where the estimated dose distribution result calculated in step 132 is outputted on the display unit as display signals, together with a planning result. The display then may be, for example, a summary including a dose volume histogram (DVH) or the like. Preferably, a comment about influences on normal organs, and others can be displayed together.

If the operator determines that this display is insufficient (improper) upon watching this display, he/she does not input "OK", and hence, the processing returns to step 107 based on the determination by step 134. Until the determination in step 134 becomes "YES", the processing of steps 107 to 134 is repeated.

If the operator determines that the created treatment planning information is proper, he/she inputs "OK", thereby satisfying the determination in step 134. Thereafter, the operator performs a registration instruction input (via a button on the screen display or keyboard) to permit the registration in the treatment planning information, thereby satisfying the determination in step 135. Then, in a next step 136, the operator performs registration processing for the treatment planning information at the storage unit 110, thus completing the processing shown in FIG. 2.

Next, the central control unit 100 reads the treatment planning information, in which divided irradiations are planned as described above and which has been stored in the storage unit 110, and stores it into the memory 103. The CPU 101 transmits, to the memory 41M of the scanning controller 41, the treatment planning information stored in the memory 103 (i.e., information such as the number of layers, the number of irradiation positions (the numbers of spots), the irradiation order with respect to irradiation positions in each of the layers, a target irradiation dose (set irradiation dose) at each irradiation position, and current values of the scanning electromagnets 5A and 5B with respect to all spots in each of the layers). The scanning controller 41 stores this treatment planning information into the memory 41M. Also, the CPU 101 transmits, to the accelerator controller 40, all data of acceleration parameters of the synchrotron 12 with respect to all layers out of the treatment planning information. The data of acceleration parameters includes the value of an exciting current for each of the electromagnets for the synchrotron 12 and beam transport system, and the value of high-frequency power to be applied to the high-frequency accelerating cavity, which are each determined by the energy of ion beam applied to each of the layers. The data of these acceleration parameters is classified, for example, into a plurality of acceleration patterns in advance.

FIG. 11 shows a part of the treatment planning information stored in the memory 41M of the scanning controller 41. The part of the information comprises irradiation parameters, that is, information on the irradiation index number (layer number and irradiation number), information on the X-direction position (X-position) and the Y-direction position (Y-position) of an irradiation position (spot), and information on a target irradiation dose (irradiation dose) for each divided irradiation. Furthermore, the irradiation parameters includes layer change flag information. The information on the irradiation number, for example, "2-2" means a "second-time irradiation in the layer 2, "2-3" means a "third-time irradiation in the layer 2", and "3-1" means a "first-time irradiation in the layer 3". The information on a X-direction position and Y-direction position is represented by current values of the scanning electromagnets 5A and 5B for scanning an ion beam to the irradiation position specified by the pertinent X-position and Y-position. Spot numbers J (described later) are given, in the irradiation order, to all divided irradiations with respect to the layer 2, i.e., "2-1" (not shown), "2-2", and "2-3". Likewise, spot numbers are given to all divided irradiations with respect to the other layers 1, 3, and 4.

Next, with reference to FIG. 12, specific descriptions will be made of respective controls by the scanning controller 41 and the accelerator controller 40 in performing the spot scanning in this embodiment. If an irradiation start instructing unit (not shown) disposed in the treatment room is operated, then in step 201, the accelerator controller 40 correspondingly initializes an operator i denoting a layer number to 1, as well as initializes an operator j denoting a spot number to 1, and outputs signals to that effect.

Upon being subjected to the initialization in step 201, the accelerator controller 40 reads and sets the accelerator parameters with respect to the i-th layer (i=1 at this point in time) out of the acceleration parameters of a plurality of patterns stored in the memory, in step 202. Then, in step 203, the accelerator controller 40 outputs it to the synchrotron 12. Also, in step 203, the accelerator controller 40 outputs exiting current information with respect to the electromagnets that is included in the i-th accelerator parameters, to the power source for each of the electromagnets of the synchrotron 12 and beam transport system 5, and controls a pertinent power source so that each of the electromagnets is excited by a predetermined current using this exiting current information. Furthermore, in step 203, the accelerator controller 40 controls the high-frequency power source for applying a high-frequency power to the high-frequency cavity to increase the frequency up to a predetermined value. This allows the energy of an ion beam circulating through the synchrotron 12 to increase up to the energy determined by the treatment plan. Thereafter, the processing advances to step 204, where accelerator controller 40 outputs an extraction preparation command to the scanning controller 41.

Upon receipt of the information on initial setting in step 201 and the extraction preparation command in step 204 from the accelerator controller 40, in step 205, the scanning controller 41 reads and sets current value data and irradiation dose data of the j-th spot (j=1 at this point in time) out of the current value data (data shown in the "X-position and Y-position" columns in FIG. 11) and the irradiation dose data (data shown in the "irradiation dose" column in FIG. 11), which are already stored in the memory 41M as described above (see FIG. 13 shown later). Similarly, regarding the aforementioned target count number stored in the memory 41M, the scanning controller 41 reads and sets data of the j-th spot (j=1 at this point in time) as well. Here, the scanning controller 41 controls a pertinent power so that the electromagnets 5A and 5B are excited by the current value of the j-th spot.

After the preparation for the irradiation to the pertinent spot has been completed in this manner, the scanning controller 41 outputs a beam extraction start signal in step 300, and controls the high-frequency applying unit 9 to extract an ion beam from the synchrotron. Specifically, the open/close switch 92 is closed by the beam extraction start signal passing through the accelerator controller 40 and a high frequency is applied to the ion beam, whereby the ion beam is extracted. Because the electromagnets 5A and 5B are excited so that the ion beam reaches the first spot position, the ion beam is applied to the first spot in a pertinent layer by the beam delivery apparatus 15. When the irradiation dose at the first spot reaches a pertinent target irradiation dose, the scanning controller 41 outputs a beam extraction stop signal in step 300. The beam extraction stop signal passes through the accelerator controller 40 and opens the open/close switch 92, thereby stopping the extraction of the ion beam.

At this point in time, only the first-time irradiation to the first spot in the layer 1 has been completed. Since the determination in step 208 is "No", the processing advances to step 209, where 1 is added to the spot number j (i.e., the irradiation position is moved to the next spot adjacent). Then, the processing of steps 205, 300, and 208 are repeated.

Specifically, until the irradiation to all spots in the layer 1 is completed, the irradiation (scanning irradiation) of ion beam is performed while moving the ion beam to adjacent spots one after another by the scanning electromagnets 5A and 5B and stopping the irradiation during movement.

If all divided irradiations to all spots in the layer 1 (seven-time irradiations in the above-described example) have been completed, the determination in step 208 becomes "Yes". At this time, the scanning controller 41 outputs a layer change command to the CPU of the accelerator controller 40. Upon receipt of the layer change command, the CPU of the accelerator controller 40 adds 1 to the layer number i (i.e., changes the object to be irradiated to the layer 2) in step 213, and outputs a remaining beam deceleration command to the synchrotron 12 in step 214. By the output of the remaining beam deceleration command, the accelerator controller 40 controls the power source for each of the electromagnets in the synchrotron 12 to gradually reduce the exciting current of each of the electromagnets until it becomes the predetermined current such as the current appropriate for the beam injection from the pre-stage accelerator. This decelerates an ion beam circulating through the synchrotron 12. As a result, the time period during which a beam can be extracted varies depending on the number of spots and irradiation dose. At the point in time, since only the irradiation with respect to the layer 1 has been completed, the determination in step 215 becomes "No". In step 202, the accelerator parameters for the second layer (layer 2) is read from the memory for the accelerator controller 40 and is set. Hereinafter, the processing of steps 203 to 215 is performed with respect to the layer 2. Also, until all divided irradiations to all spots in the layer 4 is completed, the processing of steps 202 to 215 is performed.

If the determination in step 215 becomes "Yes" (i.e., if predetermined irradiations to all spots in all layers in the target of a patient 30 have been completed), the CPU of the accelerator controller 40 outputs an irradiation end signal to the CPU 101.

As described above, under the acceleration by the synchrotron 12, an ion beam extracted from the synchrotron 12 is transported through the beam transport system. Then, the ion beam is applied to the target of the pertinent patient in an optimum mode as planned by a treatment plan, via the beam delivery apparatus 15 in the treatment room in which the patient to be irradiated is present.

At this time, a detection signal of the dose monitor 6A provided in the nozzle of the beam delivery apparatus 15 is inputted to the scanning controller 41. Other features of this embodiment are: by using this detection signal, (1) to clear the integrated value of irradiation doses simultaneously with a beam-off signal; (2) to determine the occurrence of an abnormal operation in accordance with an elapsed time after beam extraction is started; and (3) to determine the occurrence of an abnormal operation based on the comparison between the integrated value of irradiation doses and a predetermined regulated value.

More detailed explanations thereof will be provided below with reference to FIGS. 13 to 18.

FIG. 13 is a detailed functional block diagram showing the functional construction of the scanning controller 41. As shown in FIG. 13, the scanning controller 41 comprises a preset counter 41a, recording counter 41b, and maximum dose counter 41c as ones related to the detection of an irradiation dose, and for controlling these counters, comprises a preset counter control section 41A, recording counter control section 41B, and maximum dose counter control section 41C. Here, the dose monitor 6A is a known one, and of a type that outputs pulses in accordance with the amount of electrical charges ionized by the passage of beam. Specifically, the dose monitor 6A outputs one pulse for each predetermined minute charge amount. The preset counter 41a and recording counter 41b determine the irradiation dose by counting the number of pulses outputted from the dose monitor 6A.

Besides the above-described preset counter 41a, the preset counter control section 41A includes a spot timer 41Aa, difference calculating section 41Ab, determination section 41Ac, OR circuits 41Ad and 41Ae. The preset counter 41a includes a pulse input section 41aa, set value input section 41ab, initialization (clear) signal input section 41ac, operation start (START) signal input section 41ad, count value reading section 41ae, and set value comparison result output section 41af.

Besides the above-described recording counter 41b, the recording counter control section 41B includes a first delay timer 41Ba, second delay timer 41Bb, first register 41Bc, second register 41Bd, difference calculating section 41Be, determination section 41Bf, NOT circuit 41Bg, and OR circuit 41Bh. The recording counter 41b includes a pulse input section 41ba, initialization (clear) signal input section 41bc, operation start (START) signal input section 41bd, and count value reading section 41be.

As described above, the maximum dose counter control section 41C has a maximum dose counter 41c, which includes a pulse input section 41ca, set value input section 41cb, initialization (clear) signal input section 41cc, operation start (START) signal input section 41cd, and set value comparison result output section 41cf.

Furthermore, the scanning controller 41 has a memory 41M and beam extraction start/stop signal producing section 41S.

Figure 12:
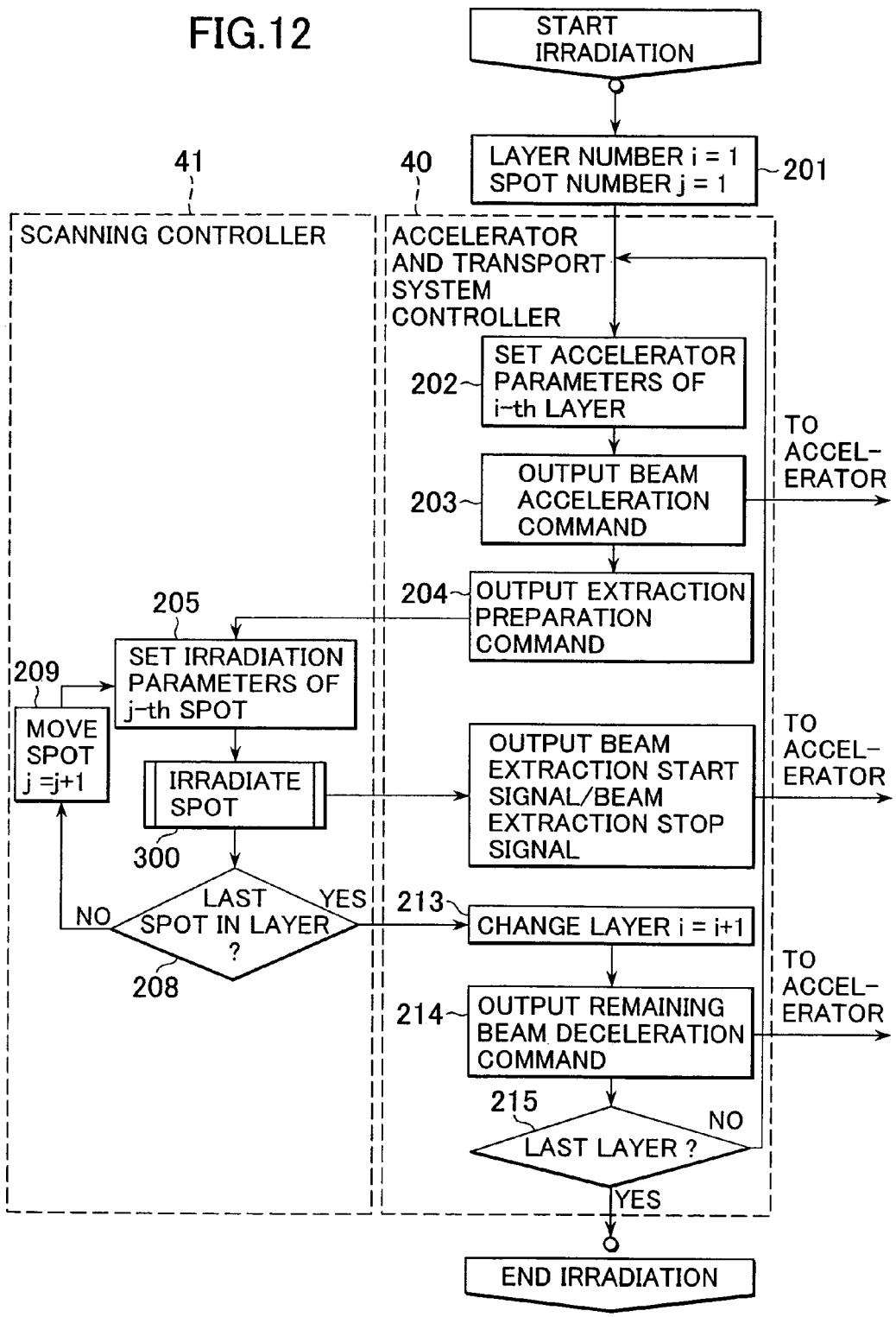
FIG. 12 is a flowchart showing the control procedure executed by the scanning controller, and accelerator and transport system controller shown in FIG. 1.
Figure 14:
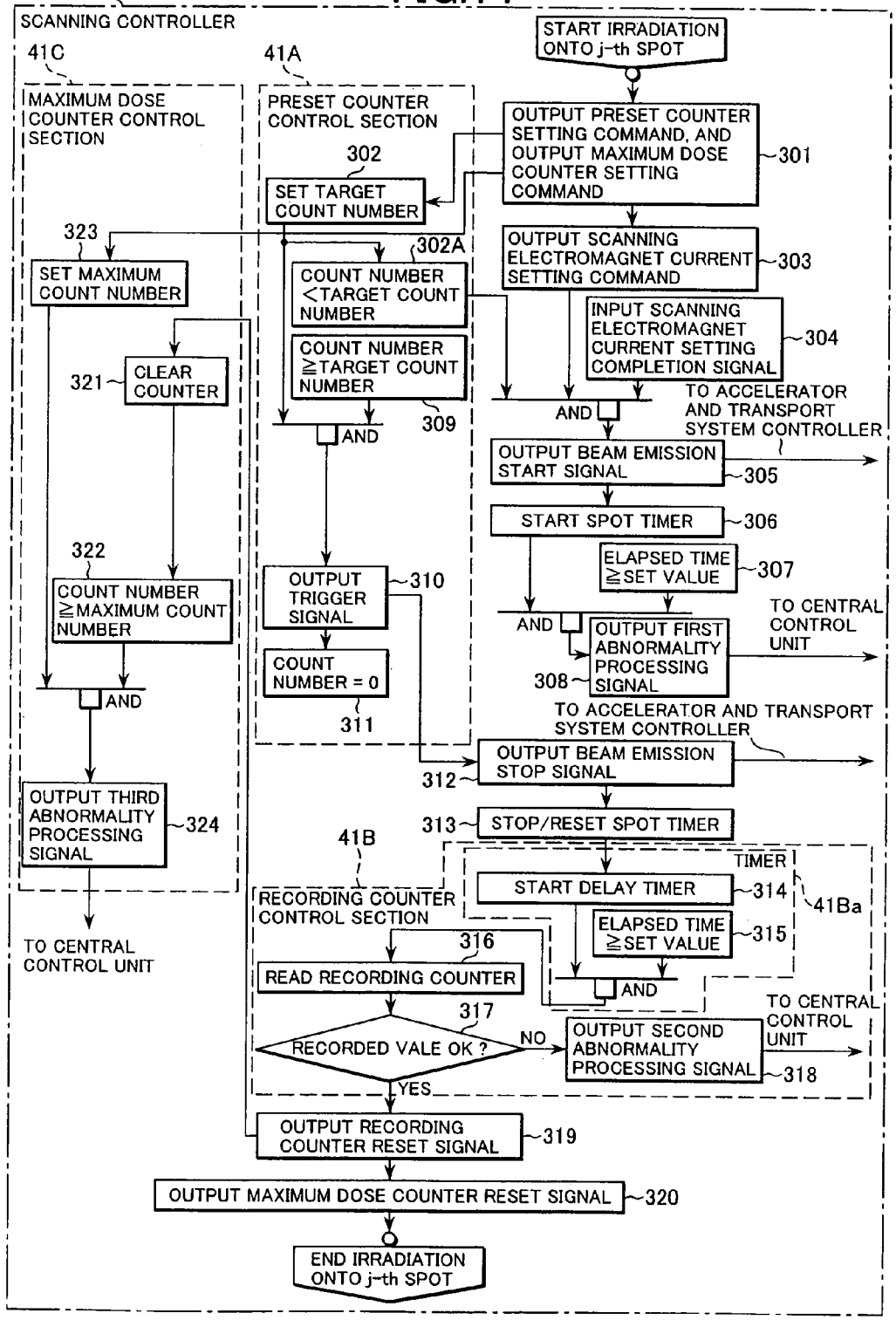
FIG. 14 is a flowchart showing details of the control procedure executed by the scanning controller shown in FIG. 1.

FIG. 14 is a flowchart showing the detailed procedures in steps 205 and 300 in FIG. 12 executed by the scanning controller 41 with the above features. As described above, the operator i is initialized to 1, and the operator j is initialized to 1, in advance. In step 301, the scanning controller 41 outputs a preset count setting command corresponding to the target count number of the preset counter 41a already stored in the memory 41M, to the preset counter set value input section 41ab of the preset counter control section 41A. In step 302, the scanning controller 41 sets a target count number at the first spot in the layer 1 in accordance with the aforementioned set command. Here, the "target count number" -refers to a value corresponding to the target irradiation dose of a pertinent spot in a pertinent layer in the column "radiation dose" shown in FIG. 11. This target count number is calculated by the scanning controller 41 based on the above-described target irradiation dose, before the start of ion beam irradiation. The calculation of the target count number using the target irradiation dose may be performed immediately after the preset counter control section 41A receives the aforementioned set command, or alternatively may be performed before the central control unit 100 transmits data to the scanning controller 41 if the central control unit 100 performs the calculation. Likewise, at this time, the scanning controller 41 outputs a maximum spot or layer dose counter setting command corresponding to the target count number (maximum dose count number) of the maximum dose counter 41c stored in the memory 41M, to the maximum dose counter set value input section 41cb of the maximum dose counter control section 41C. More details thereof will be described later.

Upon completion of step 301, the processing advances to step 303, where the scanning controller 41 outputs a current setting command with respect to the electromagnets 5A and 5B regarding a pertinent spot, i.e., current data corresponding to each of X-position and Y-position in FIG. 11, to the power source for the electromagnets 5A and 5B. The electromagnets 5A and 5B generate a deflection electromagnetic force with pertinent current values, and output a current setting completion signal indicating that such a state has been accomplished, to the scanning controller 41. In step 304, this current setting completion signal is inputted to the beam extraction start/stop signal producing section 41S.

On the other hand, in the preset counter control section 41A, when the target count number is set in step 302 as described above, this set value is inputted not only to the aforementioned preset counter set value input section 41ab but also to the difference calculation section 41Ab. Furthermore, the count number counted at this point in time (i.e., the count number at setting) is read from the preset counter count value reading section 41ae, and this is also inputted to the difference calculation section 41Ab. The difference calculation section 41Ab calculates the difference between these values: (count number at setting)−(target count number), and inputs it to the determination section 41Ac. In step 302A, the determination section 41Ac determines whether this difference is negative, namely, whether the count value at setting is less than the target count number. If this determination is satisfied, the determination section 41Ac outputs a target count number setting OK signal to the beam extraction start/stop signal producing section 41S.

In step 305, the scanning controller 41 outputs a beam extraction (radiation) start signal from the beam extraction start/stop signal producing section 41S on the conditions that the target count number setting OK signal from the determination section 41Ac of the preset counter control section 41A, the current setting command in step 303, and the current setting completion signal from the scanning electromagnets 5A and 5B have been inputted. The beam extraction start signal passes through the accelerator controller 40 and closes the open/close switch 92. An ion beam is extracted from the synchrotron 12, and the ion beam is applied to a pertinent spot (e.g., the first spot in the layer 1). Next, the processing advances to step 306, where the beam extraction start/stop signal producing section 41S outputs a timer start command signal for starting the spot timer 41Aa of the preset counter control section 41A. If the elapsed time after this start that is measured by the spot timer 41Aa becomes a predetermined set time or more, (namely, if the beam extraction is performed for a predetermined time or more without being reset, as described later), a time excess signal is issued in step 307. In step 308, on the conditions that the time exceed signal has occurred and the timer start command signal has been inputted, a first abnormality signal is outputted to the central control unit 100. Upon receipt of the first abnormality signal, the central control unit 100 performs a predetermined abnormality processing, for example, an immediate forced stop with respect to beam extraction from the synchrotron 12, and recording to that effect through the intermediary of the scanning controller 41 and accelerator controller 41 (or alternatively, not through the intermediary thereof).

On the other hand, when a beam irradiation is started by the output of the beam extraction start signal in step 305, detection signal of the dose monitor 6A is converted into a train of dose pulses by a current-frequency converter (i.e., I-F converter; not shown), and thereafter they are inputted to the preset counter pulse input section 41aa, recording counter pulse input section 41ba, maximum dose counter pulse input section 41ca of the scanning controller 41. These counters 41a, 41b, and 41c simultaneously count the pulses. This count number represents the irradiation dose from the start of counting.

If the count value based on the input pulses from the pulse input section 41aa becomes a value of no less than the set value of the target count number set in step 302, the preset counter 41a issues an irradiation dose excess signal in step 309. In step 310, on the conditions that the irradiation dose excess signal has occurred and the target count number set in step 302 has been inputted, the preset counter 41a outputs a trigger signal from the set value comparison result output section 41af. As a first reset signal, this trigger signal is inputted to the initialization (clear) signal input section 41ac and operation start (START) signal input section 41ad of the preset counter 41a via the OR circuits 41Ad and 41Ae, and in step 311, the count number of the preset counter 41a is reset to start recounting.

In step 312, based on the above-described trigger signal, the beam extraction start/stop signal producing section 41S of the scanning controller 41 produces a beam extraction start/stop signal and outputs it to the accelerator controller 40. The beam extraction start/stop signal passes through the accelerator controller 40 and reaches the open/close switch 92. Substantially by the beam extraction start/stop signal, the scanning controller 41 controls the open/close switch 92 to open. This stops the extraction of the ion beam from the synchrotron 12, and stops application of the ion beam to a patient. With the stoppage of the irradiation, the beam extraction start/stop signal producing section 41S outputs a command signal to stop or reset the spot timer 431Aa in step 313.

Figure 16:
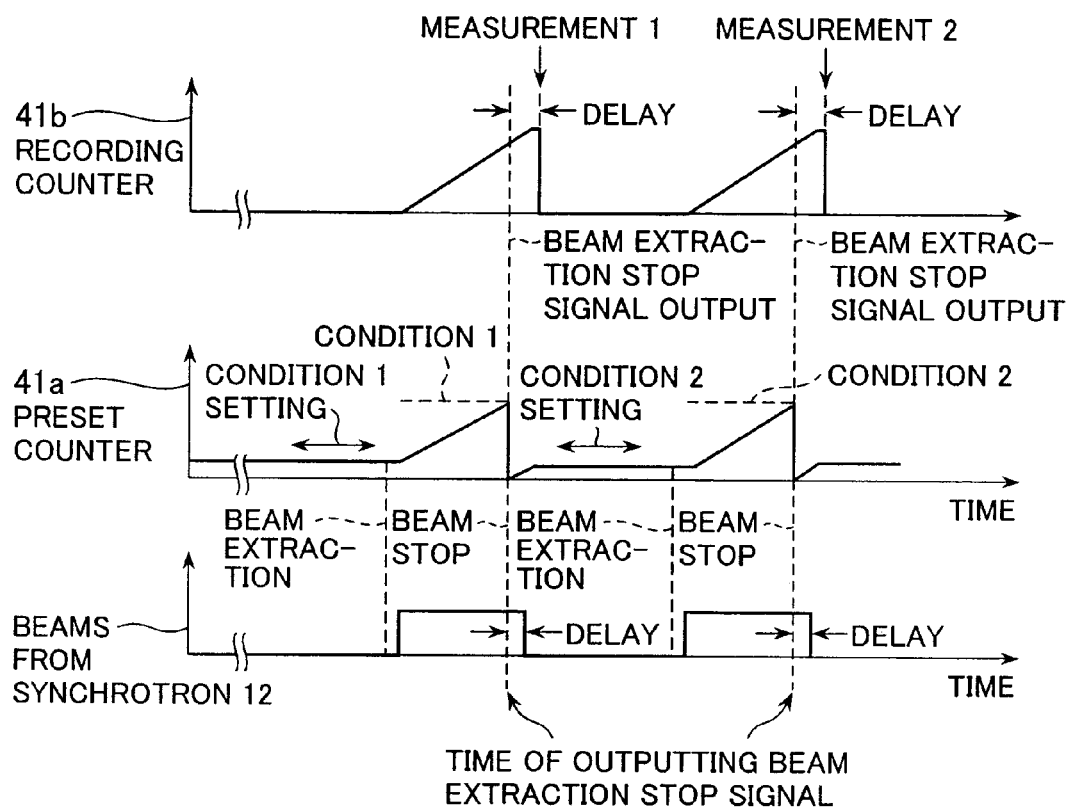
FIG. 16 is a timing chart showing an example of operations of a preset counter and recording counter as well as actual beam operations realized by the control procedures executed by a preset counter control section and recording counter control section shown in FIG. 14.

The recording counter control section 41B of the scanning controller 41 has a first and second delay timers 41Ba and 41Bb. In step 314, the above-described beam extraction start/stop signal outputted by the beam extraction start/stop signal producing section 41S is inputted as a command signal for starting the first delay timer 41Ba in the form of converting beam ON→OFF switching into OFF→ON switching via the NOT circuit 41Bg. If the elapsed time after this start becomes a predetermined set time (i.e., first delay time, corresponding to the "delay" in FIG. 16 shown later), a first time arrival signal is sent to the first register 41Bc of the recording counter control section 41B, in step 315. In step 316, on the conditions that the first time arrival signal and a first delay timer start command signal have been inputted, a recording counter reading signal is outputted from the first register 41Bc to the recording counter 41Bc, and the count value then is inputted from the recording counter count value reading section 41be to the first register 41Bc. While not shown in FIG. 14 for the sake of simplification, the above-described time arrival signal is inputted as a signal for starting the second delay timer 41Bb. As in the case of the first delay timer, if the elapsed time after the start becomes a predetermined set time (i.e., a second delay time), a second time arrival signal is sent to the second register 41Bd of the recording counter control section 41B. On the conditions that the second time arrival signal and second delay timer start command signal have been inputted, a recording counter reading signal is outputted from the second register 41Bd to the recording counter 41b, and the count value then is inputted from the recording counter count value reading section 41be to the second register 41Bd.

The count values at the first and second registers 41Bc and 41Bd are inputted to the difference calculation section 41Be, and after the difference therebetween is calculated, the difference is inputted to the determination section 41Bf.

In step 317, the determination section 41Bf of the recording counter control section 41B determines whether the recording count value is a normal value, i.e., whether the above-described difference is within a predetermined proper range, and if the determination section 41Bf determines that the difference is an abnormal value, it outputs a second abnormality signal to the central control unit 100 in step 318. Upon receipt of the second abnormality signal, the central control unit 100 executes the predetermined abnormality processing as described above. If it is determined that the difference is a normal value in step 317, the determination section 41Bf inputs a second reset signal for resetting the recording counter 41b to the initialization (clear) signal input section 41bc and operation start (START) signal input section 41bd of the recording counter 41b via the OR circuit 41Bb, and after the resetting, starts recounting in step 319. Also, the count value then is outputted as an actual dose record from the determination section 41Bf to the central control unit 100. Furthermore, in step 320, the determination section 41Bf outputs a third reset signal for resetting the maximum dose counter control section 41C to the initialization (clear) signal input section 41cc and operation start (START) signal input section 41cd of the maximum dose counter 41c via the OR circuit 41Bb.

On the other hand, based on the third reset signal inputted to the initialization (clear) signal input section 41cc and operation start (START) signal input section 41cd, the maximum dose counter 41c clears the count value and then starts recounting in step 321. If the beam extraction start signal is outputted in step 305, the maximum dose counter 41c counts pulses as a detection signal of the dose monitor 6A inputted to the pulse input section 41ca of the maximum dose counter 41c. This counter number represents the irradiation dose from the start of counting. In this time, in step 323, the maximum dose counter 41c has set a target count number (maximum dose count number) in a pertinent spot to be irradiated, in accordance with a maximum dose counter setting command inputted to the set value input section 41cb in the above-described step 301. If the above-described integrated value of irradiation dose becomes a value of no less than the set value of the target maximum count number set in the above step 323, the maximum dose counter 41c produces a count excess signal in step 322. Then, in step 324, on the conditions that the set target maximum count number (step 323) and the count excess signal has been inputted, the maximum dose counter 41c outputs a third abnormality signal from the set value comparison result output section 41cf to the central control unit 100 in step 324. Upon receipt of the third abnormality signal, the central control unit 100 executes the above-described predetermined abnormality processing. The target maximum count number refers to an irradiation dose set so as to be a little larger than the largest target dose in respective target irradiation doses with respective to all irradiation positions (all spots) in a target.

Figure 15:
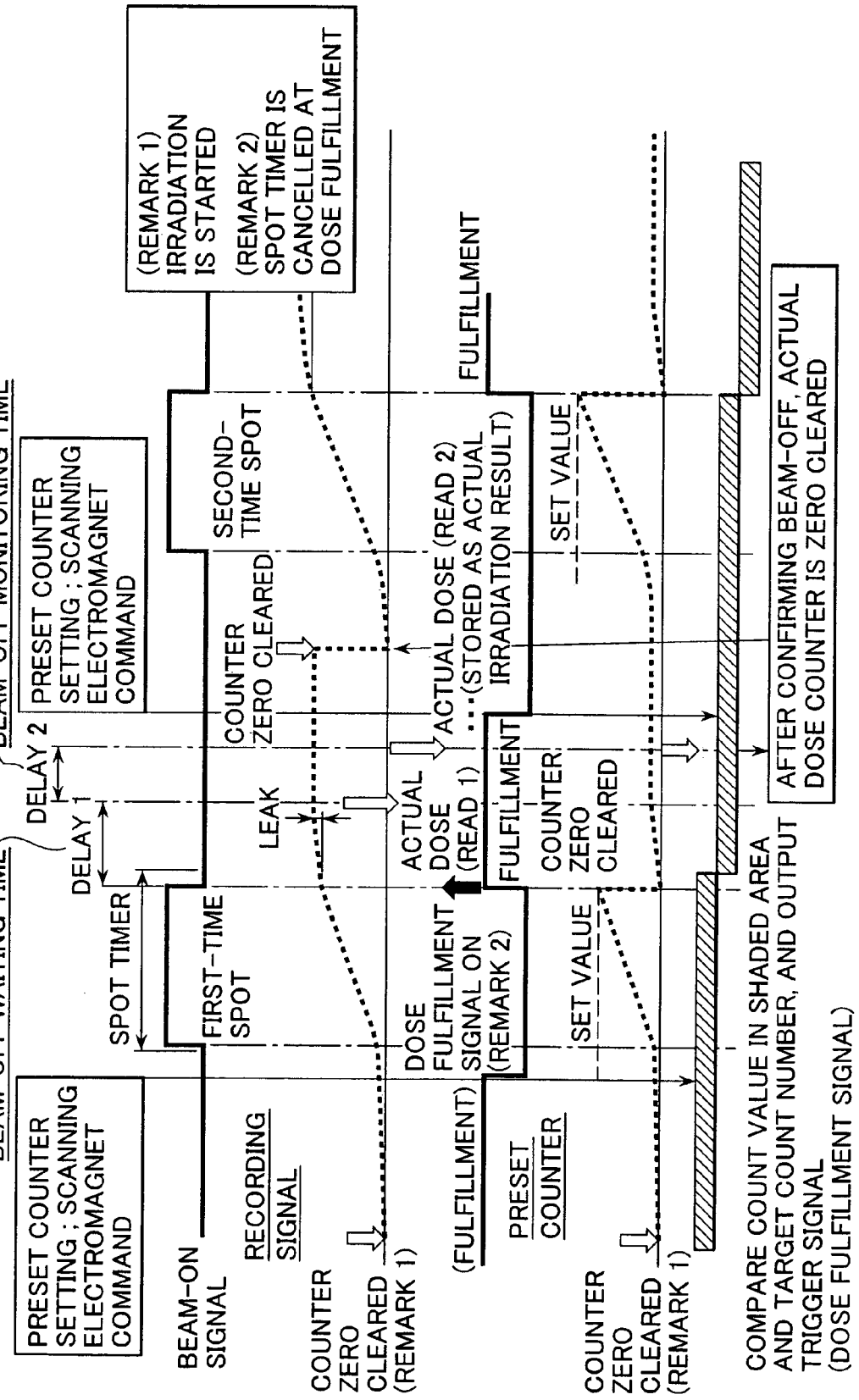
FIG. 15 is a timing chart illustrating operations of the recording counter and preset counter shown in FIG. 13.

FIG. 15 is a timing chart showing a series of operations of the preset counter 41a and recording counter 41b as described above.

According to the particle beam treatment system of this embodiment with the above-described features, the following effects are provided.

(1) Resolution Enhancing Effect by Divided Irradiations

In general, the position monitor 6B is of a type that accumulates electric charges ionized by the passage of an ion beam in a capacitor and that reads a voltage induced in the capacitor after the spot irradiation. The capacity of this capacitor is determined so as to permit the amount of ionized electric charges by the spot subjected to the maximum irradiation dose. Regarding this capacitor, as the capacity decreases, the output voltage increases and the signal-to-noise ratio becomes higher, thereby enhancing the position measurement resolution. Conversely, as the capacity increases, the resolution decreases.

Accordingly, in this embodiment, in a treatment plan using the treatment planning unit 140, it is planned that the irradiation to each spot in a layer is performed by dividing it into a plurality of times of irradiations (for example, in the example shown in FIG. 7, irradiations are performed seven times in the layer 1, three times in the layer 2, two times in the layer 3, and two times in the layer 4). The central control unit 100, accelerator controller 40, and scanning controller 41 control the synchrotron 12 and beam delivery apparatus 15 by using treatment information obtained by the above treatment plan. By virtue of this feature, regarding an irradiation position subjected to too much irradiation dose by one-time ion beam irradiation, it is possible to perform a divided irradiation so as to reduce an irradiation dose for each divided irradiation. This allows the difference in irradiation dose between the irradiation position subjected to the maximum dose and that subjected to the minimum dose to be reduced, thereby leveling off irradiation dose. In the example in FIG. 7, the maximum radiation dose is 10 at the spots in the layer 1, while the minimum radiation dose is 6.3 at the spots in the layer 4. As a result, the capacity of the capacitor of the position monitor 6B can be correspondingly reduced to enhance the resolution. This makes it possible to further correctly detect an actual beam position during treatment.

(2) High-Accuracy Irradiation Effect by Preset Counter Clear

In this type of particle beam irradiation apparatus, in order to reduce the exposure of normal tissue to radiation to a minimum and perform a proper treatment with neither too much nor too little irradiation, there is usually provided an irradiation dose monitor for measuring the irradiation dose of ion beam. When performing irradiation to each spot, a target irradiation dose is set on a spot-by-spot basis. Once the integrated value of irradiation doses detected by the dose monitor has reached the target value, a beam extraction stop command signal (beam stop command) is outputted to the accelerator, and in response to it, the accelerator stops the extraction of charged particle beam. With typical accelerator such as a slow cycling synchrotron or a cyclotron, even if the beam stop command is inputted, strictly speaking, it is not impossible that some amount of response delay occurs rather than the output of the charged particle beam immediately stops.

In view of the above problem, in this embodiment, once the irradiation dose detected by the dose monitor 6A and counted by the preset counter 41*a* has reached a predetermined value, i.e., a target value (see step 309), the preset counter control section 41A outputs a trigger signal for triggering the scanning controller 41 to output the beam extraction stop signal to the high-frequency applying unit 9 (see step 312), and in step 311, clears the integrated count number of the preset counter 41*a* to restart integration, without waiting for the actual stop of the beam from the accelerator.

FIG. 16 is a time chart showing the operations at this time. As shown in FIG. 16, a response delay can occur between the outputting of the beam extraction stop signal and the actual stoppage of the ion beam extraction from the synchrotron 12. During this response delay, the irradiation dose of ion beam extracted from the synchrotron 12 is integrated after the aforementioned clearing. After the extraction of ion beam has been actually stopped, the irradiation position is changed to a next irradiation position (spot) by the processing in steps 209 and 205 (see FIG. 12), and in step 302, the target count number is changed (in FIG. 16, for example, a change from the condition 1 (the target irradiation dose to be applied to the spot situated at a position) to the condition 2 (the target irradiation dose to be applied to the next spot) is made). Here, the target count number is a count number corresponding to a target irradiation dose. In step 303, the scanning electromagnets 5A and 5B are subjected to control, and in 305, the extraction of ion beam from the synchrotron 12 is restarted. At this time, the irradiation dose at the aforementioned next spot after the beam has moved there is detected by the dose monitor 6A and integrated by the preset counter 41*a*, like the foregoing. The integration of count number then includes previously, as an initial value, the count number with respect to an immediately preceding spot during the time period of the response delay of the accelerator, and the irradiation dose at the spot subsequent to the aforementioned spot is added to this initial value (see the part "condition 2 setting" in FIG. 16). As a result, irradiating the above-described subsequent spot with ion beam extracted from the synchrotron 12 until a target irradiation dose is reached, means irradiating this spot with the irradiation dose obtained by subtracting the aforementioned initial value from the target irradiation dose at this spot (i.e., the irradiation dose shown in "condition 2" in FIG. 16). Once the irradiation dose at this spot after the movement has reached a target irradiation dose, the preset counter control section 40A outputs a trigger signal for triggering the scanning controller 41 to output the beam extraction stop signal to the high-frequency applying unit 9, and clears the count number of the preset counter 41*a*, like the foregoing. The irradiation dose during the time period of the response delay of the synchrotron 12 is added as an initial value in irradiating the spot after a further subsequent movement, and the same is repeated hereinafter.

Figure 17:
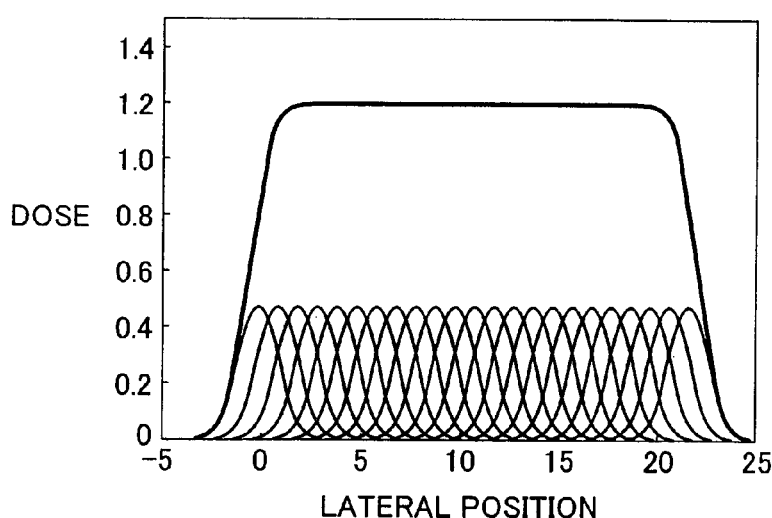
FIG. 17 is a diagram showing an example of irradiation dose distribution realized by a comparative example in the present invention, the comparative example corresponding to the conventional art.
Figure 18:
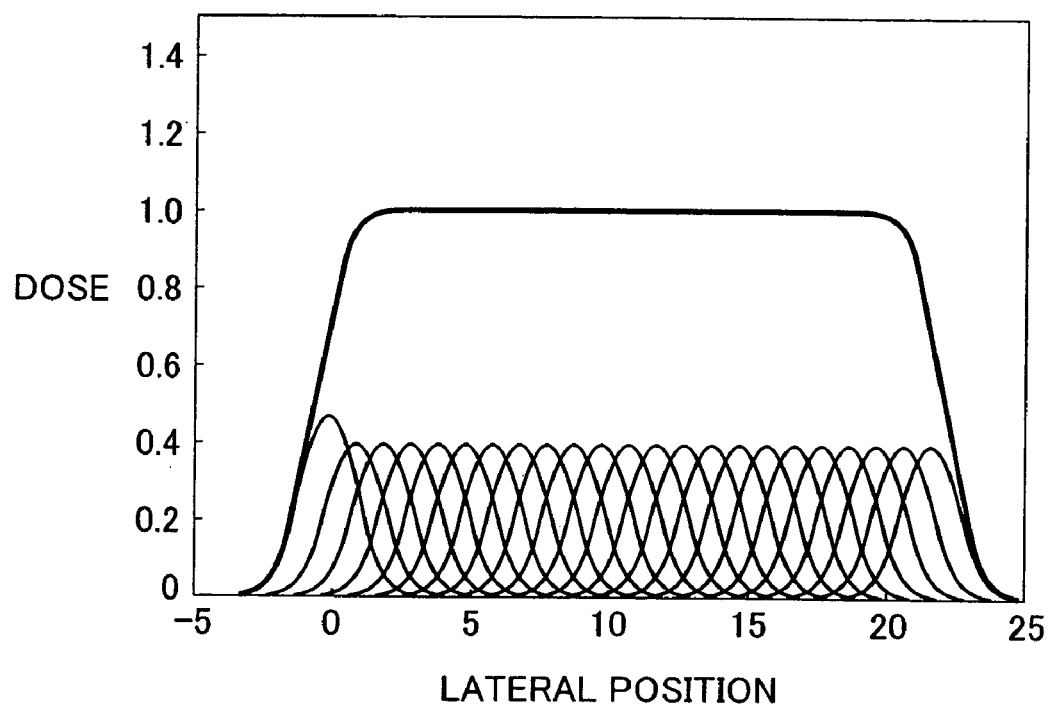
FIG. 18 is a diagram showing an example of irradiation dose distribution realized by the control procedures executed by the preset counter control section and recording counter control section shown in FIG. 14.

Because the scanning controller 41 performs the above-described control, when attempting to irradiate each spot, an ion beam is always applied to the spot until the target dose of the spot is reached, on the assumption that an irradiation dose for the time period during a response delay of the synchrotron 12 occurring at irradiation to a spot is a part of irradiation dose at a subsequent spot. If irradiation dose control is performed without giving consideration to the response delay, an excessive irradiation corresponding to response delay is performed. This raises the possibility that the irradiation dose becomes, e.g., 1.2 at all spots (the intended irradiation dose is represented by 1.0 as shown in FIG. 17). In contrast, in this embodiment, by performing the above-described control, an ion beam dose (nearly equals 1.0) substantially equal to the target irradiation dose set with respect to a pertinent spot can be applied to all spots except the first spot to be irradiated (i.e., the spot at the left end in FIG. 18) with high accuracy, without an excessive irradiation corresponding to a response delay.

In this embodiment, based on the assumption that the irradiation dose corresponding to a response delay of the synchrotron 12 occurring when irradiating a pertinent spot is a part of the irradiation dose at a next spot, an ion beam is applied to the pertinent spot until the target dose at the pertinent spot is reached. However, the same effect can be obtained using the following methods (1) and (2), as well.

(1) To output a trigger signal in step 310 based on the conditions that, in step 309 in the preset counter control section 41A, when, from the target irradiation dose at a spot, the irradiation dose corresponding to the response delay occurring when irradiating immediately preceding spot is subtracted, and further when from the remaining irradiation dose, the count number with respect to the spot during irradiation is subtracted, remaining irradiation dose has become zero, and that the set target count number has been inputted in step 302.

(2) To set the irradiation dose obtained by, from the target irradiation dose on a spot, subtracting the irradiation dose corresponding to the response delay occurring at the time of irradiating immediately preceding spot, as the target count number set in step 302 in the preset counter control section 41A.

(3) Safety Enhancing Effect by Spot Timer

Since the dose monitor 6A is an machine, it is difficult to perfectly eliminate the possibility that the irradiation dose monitor causes a malfunction or failure. Also, since the target irradiation dose for each spot is usually a value transmitted from a data base or a value calculated based on the transmitted value, it is not impossible that an improper value is inputted at the stage of the transmission or the calculation.

In light of the above, in this embodiment, the scanning controller 41 has a spot timer, and determines whether an abnormal operation has occurred in accordance with the elapsed time after an ion beam started to be extracted to one spot (see steps 306 and 307 in FIG. 14). If the elapsed time after the extraction start becomes no less than a predetermined time, the scanning controller 41 outputs an abnormality signal for indicating the occurrence of an abnormal operation (the first abnormality signal) in step 308. Therefore, even if the extraction time of the charged particle beam is likely to abnormally elongate due to a malfunction or an occurrence of failure of the dose monitor 6A, or improper input value, the extraction of ion beam can be stopped after a certain time has elapsed. This reliably prevents excessive irradiation to an affected part, and further improves the safety.

(4) Safety Enhancing Effect by Maximum Dose Counter

Regarding the function of stopping the output of ion beam when the irradiation dose detected by the dose monitor reaches the target value, it is not impossible that equipment associated with this function causes a malfunction or failure. Also, it is not impossible that an error occurs in the setting of irradiation data.

In view of the above problems, in this embodiment, the maximum dose counter control section 41C in the scanning controller 41 determines whether any abnormal operation has occurred (see steps 322 and 323 in FIG. 14) in accordance with the magnitude relation between the count number detected by the dose monitor 6A and integrated by the maximum dose counter control section 41C and a predetermined regulated value. If the count number becomes no less than a predetermined regulated value, the scanning controller 41 outputs a third abnormality signal in step 324. Therefore, even if the ion beam does not readily to stop due to a malfunction or the like of the beam stopping function and the irradiation dose is likely to abnormally increase, the irradiation can be stopped at a certain upper limit irradiation dose, thereby reliably preventing an excessive irradiation to an affected part. This further enhances the safety.

Also, even if a target irradiation dose abnormally increases due to a malfunction or the like of data communications when an operator directly manually makes a regulated value a set value using, e.g., a hard switch, and the charged particle beam does not readily stop due to a malfunction or the like of the beam stopping function and the irradiation dose is likely to abnormally increase, the irradiation can be stopped at a certain upper limit irradiation dose, thereby reliably preventing an excessive irradiation to an affected part. This further enhances the safety.

(5) Deceleration Effect of Ion Beam Remained in Synchrotron at Completion of Irradiation to All Spot in Layer In the spot scanning irradiation according to the present invention, as the size of a target changes, the number of spots in a layer changes, and consequently, the time required to complete an irradiation to all spots in the layer changes. Regarding the allowable extraction period of synchrotron, if it is set to be long with a large target assumed, the irradiation to all layers takes much time to complete, thereby elongating the treatment time for a patient. In view of the above, in this embodiment, after the irradiation to all spots in a layer has been completed, the charged particle beam in the accelerator is decelerated, quickly outputs a remaining beam deceleration command, thereby decelerating ion beams in the synchrotron. This terminates the allowable extraction period of the synchrotron. As a result, the allowable extraction period is controlled to a requisite minimum, thereby making the treatment time with respect to a patient short.

Figure 19:
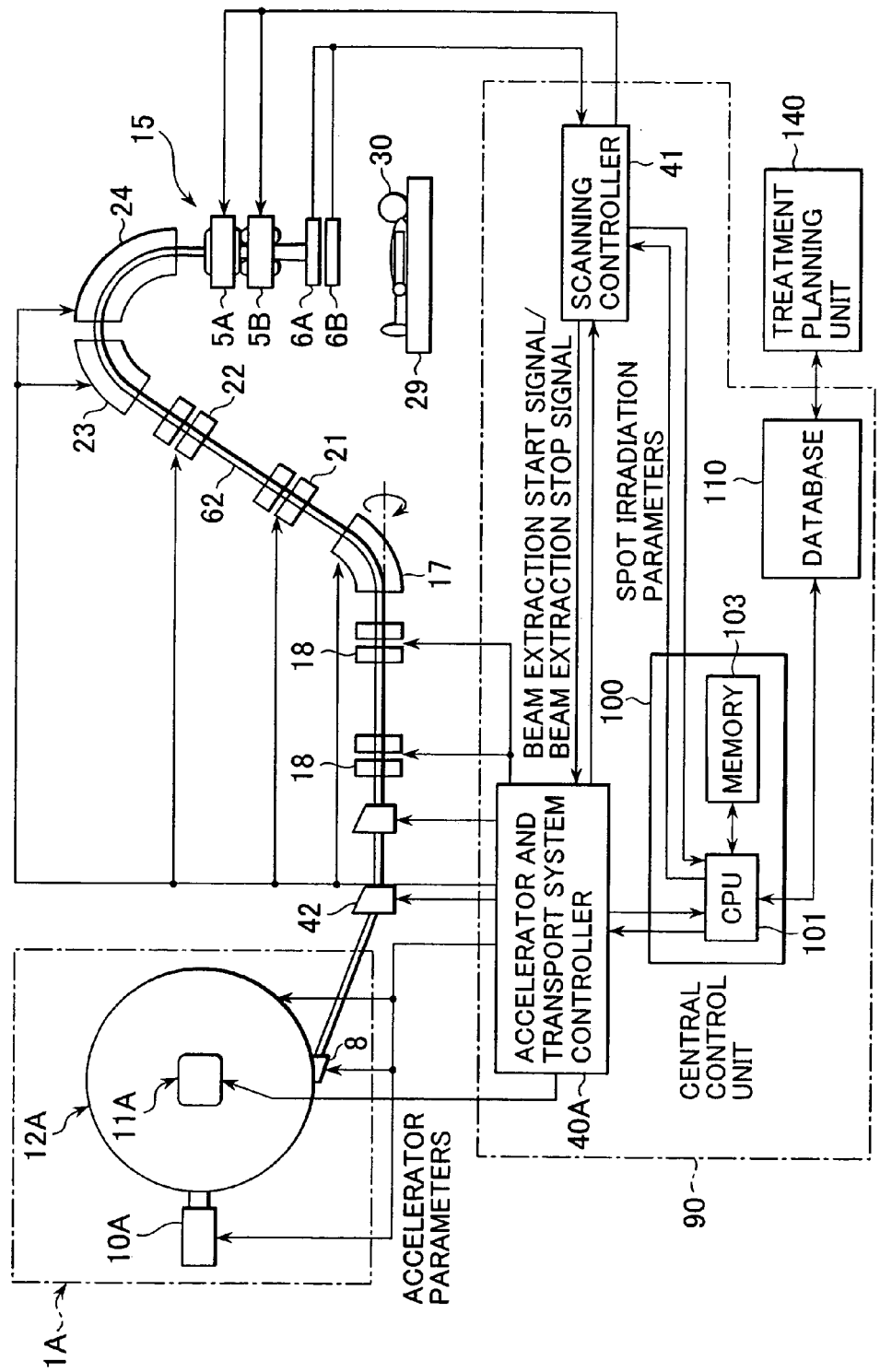
FIG. 19 is a schematic diagram of the overall construction of a particle beam irradiation apparatus according to another embodiment of the present invention.

The above-described ion beam irradiation by spot scanning can be applied to a proton beam treatment system using a cyclotron serving as an accelerator. This proton beam treatment system will be explained with reference to FIG. 19. The proton beam treatment system according to this embodiment has a construction where, in the proton beam treatment system shown in FIG. 19, the synchrotron is changed to a cyclotron 12A, and an energy changing unit (a second element and a charged particle beam energy changing unit) 42 is newly added. A charged particle beam generating unit 1A has a cyclotron 12A, which accelerates ion beams of the fixed energy. The cyclotron 12A has an acceleration unit 10A. The charged particle beam energy changing unit 42 is installed to a beam transport system 4 in the vicinity of the cyclotron 12A. The energy changing unit 42 comprises a plurality of planar degraders (not shown) for passing ion beams therethrough to cause the ion beams to lose energy, bending electromagnets (not shown) for deflecting the ion beams, which have been reduced in energy, and an aperture (not shown) for cutting out a part of the ion beams after passing the bending electromagnets. The energy changing unit 42 further includes a plurality of energy adjusting plates having thicknesses different from each other for changing energy value. Ion beams are changed in energy value by passing through the degraders. The plurality of degraders are made different in thickness from each other in order to obtain a plurality of energy values.

As in the case of the embodiment shown in FIG. 1, the CPU 101 in the central control unit 100 reads the treatment planning information (see FIG. 11) stored in the memory 103 from the storage unit 110, and causes the memory (not shown) in the scanning controller 41 to store it. The CPU 101 transmits to an accelerator controller 40A all of data of operational parameters concerning all layers out of the treatment planning information. Here, the data of operational parameters comprises degrader numbers and an exciting current value of each electromagnets in the beam transport system, which are determined by the energy of ion beams applied to each of the layers.

The control by the scanning controller 41 during the spot scanning according to this embodiment is performed similarly to the control illustrated in FIGS. 12 and 14 in the embodiment shown in FIG. 1. The control by the accelerator controller 40A is the control by the accelerator controller 40 shown in FIG. 12 except for step 214. Therefore, the accelerator controller 40A executes step 215 after step 213. Here, out of the control by the accelerator controller 40A, the control specific to this embodiment will be chiefly explained. In step 202, the aforementioned data of operational parameters with respect to an i-th layer (e.g., the layer 1) is set. In step 203, the accelerator controller 40A outputs degrader numbers to the energy changing unit 42, and outputs each exciting current value to a respective one of electromagnet power sources in the beam transport system 4. Specifically, the accelerator controller 40A performs control to insert a predetermined degrader in the energy changing unit 42 into beam path 62 based on the degrader number, and based on each of the exciting current values control, it perform to cause corresponding electromagnet power sources to excite a respective one of electromagnets (first element) in the beam transport system 4. The entrance of ion beam into the cyclotron 12A is performed by an ion source 11A.

The beam extraction start signal outputted from the scanning controller 41 in step 300, and more specifically in step 305 (see FIG. 14), is inputted to the power source for the ion source 11A through the accelerator controller 40A. Based on the beam extraction start signal, the scanning controller 41 activates the ion source 11A to apply ion beams to the cyclotron 12A. When the beam extraction start signal passes through the inside of the accelerator control unit 40A, the accelerator control unit 40A outputs a predetermined high-frequency power set value to the high-frequency power source (not shown) of the acceleration unit 10A. Then, the ion beam in the cyclotron 12 is accelerated to the predetermined energy and extracted from the cyclotron 12A through an extraction deflector 8. The energy of the ion beam is reduced to the set energy by the degrader provided in the beam path 62, and reaches the beam delivery apparatus 15 through the beam path 62. These ion beam is applied to the pertinent spot in a pertinent layer in the target region of a patient 30 by scanning of the scanning electromagnets 5A and 5B.

When the irradiation dose measured by the dose monitor 6A reaches a target dose of the pertinent spot, the scanning controller 41 outputs a beam extraction stop signal in step 300, and specifically in step 312 (see FIG. 14). The beam extraction stop signal is inputted to the power source for the ion source 11A through the accelerator controller 40A. Based on the beam extraction stop signal, the scanning controller 41 performs control to stop the ion source 11A and stop the application of the ion beam to the cyclotron 12A. When the beam extraction start signal passes through the inside of the accelerator control unit 40A, the accelerator control unit 40A controls the high-frequency power source for the acceleration unit 10A to stop the application of a high-frequency power to the acceleration unit 10A. This terminates the irradiation of ion beam with respect to the pertinent spot. Hereinafter, the irradiation of ion beam with respect to a subsequent spot is performed in the same manner as in the embodiment shown in FIG. 1.

According to this embodiment, the effects (1) to (4) produced in the embodiment shown in FIG. 1 can be achieved.

As is evident from the foregoing, according to the present invention, the detection accuracy with respect to an actual irradiation dose during treatment using charged particle beams can be enhanced.

Also, according to the present invention, the control accuracy with respect to irradiation dose of charged particle beams can be improved.

Furthermore, according to the present invention, the excessive irradiation of charged particle beams due to a monitor abnormality, input error, or the like can be reliably prevented.

Moreover, according to the present invention, the excessive irradiation of charged particle beams due to a malfunction of a beam stopping function, or the like can be reliably prevented.

Besides, according to the present invention, the treatment time with respect to a patient can be reduced.

What is claimed is:

1. A particle beam emitting apparatus comprising:
   an accelerator for extracting a charged particle beam;
   a beam delivery apparatus having a charged particle beam scanning unit and irradiating the charged particle beam extracted from the acceleration;
   an irradiation dose detector that detects the irradiation dose of the charged particle beam applied to an irradiation position in a target; and
   a controller that controls the irradiation of the charged particle beam to the irradiation position so that the irradiation dose applied to the irradiation position becomes a set irradiation dose, in a state where the irradiation dose applied to the irradiation position during the time period from the outputting of a beam extraction stop signal at the time when the irradiation dose detected by the irradiation dose detector reaches the set irradiation dose up to the extraction stop of the charged particle beam from the accelerator, is added.

2. The particle beam emitting apparatus according to claim 1, wherein the controller stops the irradiation of a charged particle beam from the beam delivery apparatus, and wherein, in a state where the irradiation of the charged particle beam is stopped, the controller controls the charged particle beam scanning unit to change the irradiation position, and to start the irradiation of the charged particle beam from the beam delivery apparatus after said change.

3. The particle beam emitting apparatus according to claim 2, wherein the controller controls the charged particle beam scanning unit to perform irradiations of the charged particle beam with respect to at least one said irradiation position a plurality of times based on treatment planning information.

4. The particle beam emitting apparatus according to claim 1, wherein the controller outputs a beam extraction stop signal to thereby perform control to stop the extraction of the charged particle beam from the accelerator.

5. A particle beam emitting apparatus comprising:
   an accelerator for extracting a charged particle beam;
   a beam delivery apparatus having a charged particle beam scanning unit and irradiating the charged particle beam extracted from the acceleration;
   an irradiation dose detector that detects an irradiation dose of the charged particle beam applied to the irradiation position in a target; and
   a controller that controls the irradiation of the charged particle beam to the irradiation position so that the irradiation dose obtained by adding the irradiation dose applied to the irradiation position by the charged particle beam extracted again from the accelerator, to the irradiation dose applied to the irradiation position of the charged particle beam during the time period from the outputting of a beam extraction stop signal at the time when the irradiation dose detected by the irradiation dose detector reaches a set irradiation dose up to the extraction stop of the charged particle beam from the accelerator, becomes the set irradiation dose.

6. The particle beam emitting apparatus according to claim 5, wherein the controller stops the irradiation of a charged particle beam from the beam delivery apparatus, and wherein, in a state where the irradiation of the charged particle beam is stopped, the controller controls the charged particle beam scanning unit to change the irradiation position, and to start the irradiation of the charged particle beam from the beam delivery apparatus after said change.

7. The particle beam emitting apparatus according to claim 6, wherein the controller controls the charged particle beam scanning unit to perform irradiations of the charged particle beam with respect to at least one said irradiation position a plurality of times based on treatment planning information.

8. The particle beam emitting apparatus according to claim 5, wherein the controller outputs a beam extraction stop signal to thereby perform control to stop the extraction of the charged particle beam from the accelerator.

9. A particle beam emitting apparatus comprising:
an accelerator for extracting a charged particle beam;
a beam delivery apparatus having a charged particle beam scanning unit and irradiating the charged particle beam extracted from the acceleration;
an irradiation dose detector that detects the charged particle beam applied to an irradiation position in a target and that outputs a pulse signal; and
a controller that counts pulses of a pulse signal outputted from the irradiation dose detector due to the charged particle beam applied to the irradiation position, that stores the count number of the pulses, that clears the count number when the count number reaches a set count number, and that controls the irradiation of the charged particle beam to another irradiation position situated next to said irradiation position so that the count number with respect to said other irradiation position become a set count number, in a state where the count number of the pulses of the pulse signal generating due to the charged particle beam applied to the irradiation position during the time period from the time when the count number reaches the set count number up to the time when the extraction stop of the charged particle beam from the accelerator, is added.

10. The particle beam emitting apparatus according to claim 9, wherein the controller stops the irradiation of a charged particle beam from the beam delivery apparatus, and wherein, in a state where the irradiation of the charged particle beam is stopped, the controller controls the charged particle beam scanning unit to change the irradiation position and to start the irradiation of the charged particle beam from the beam delivery apparatus after said change.

11. The particle beam emitting apparatus according to claim 10, wherein the controller controls the charged particle beam scanning unit to perform irradiations of the charged particle beam with respect to at least one said irradiation position a plurality of times based on treatment planning information.

12. The particle beam emitting apparatus according to claim 9, wherein the controller outputs a beam extraction stop signal to thereby perform control to stop the extraction of the charged particle beam from the accelerator.

13. A method for irradiating a charged particle beam extracted by an accelerator from a beam delivery apparatus having a charged particle beam scanning unit, the method comprising the steps of:
detecting the irradiation dose of the charged particle beam applied to the irradiation position in a target; and
irradiating the charged particle beam from the beam delivery apparatus to the irradiation position until the irradiation dose at the irradiation position becomes a set irradiation dose, in a state where the irradiation dose applied to the irradiation position during the time period from the outputting of a beam extraction stop signal at the time when the detected irradiation dose reaches the set irradiation dose up to the extraction stop of the charged particle beam from the accelerator, is added.

14. A method for irradiating a charged particle beam extracted by an accelerator from a beam delivery apparatus having a charged particle beam scanning unit, the method comprising the steps of:
detecting the irradiation dose of the charged particle beam applied to the irradiation position in a target; and
irradiating the charged particle beam from the beam delivery apparatus to the irradiation position until the irradiation dose obtained by adding the irradiation dose applied to the irradiation position by the charged particle beam extracted again from the accelerator, to the irradiation dose applied to the irradiation position of the charged particle beam during the time period from the outputting of a beam extraction stop signal at the time when the detected irradiation dose reaches a set irradiation dose up to the extraction stop of the charged particle beam from the accelerator, becomes the set irradiation dose.

* * * * *